United States Patent
Reed et al.

(10) Patent No.: US 10,872,682 B2
(45) Date of Patent: Dec. 22, 2020

(54) METHOD FOR DESIGNING ALLOYS

(71) Applicant: Oxford University Innovation Limited, Oxford (GB)

(72) Inventors: Roger Reed, Oxford (GB); Zailing Zhu, Oxford (GB); David Crudden, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 426 days.

(21) Appl. No.: 15/563,100

(22) PCT Filed: Mar. 23, 2016

(86) PCT No.: PCT/GB2016/050810
§ 371 (c)(1),
(2) Date: Sep. 29, 2017

(87) PCT Pub. No.: WO2016/156805
PCT Pub. Date: Oct. 6, 2016

(65) Prior Publication Data
US 2018/0082044 A1  Mar. 22, 2018

(30) Foreign Application Priority Data
Apr. 1, 2015  (GB) .................................. 1505652.6

(51) Int. Cl.
*G01N 33/48* (2006.01)
*G01N 33/50* (2006.01)
*G16C 20/30* (2019.01)
*C22C 19/00* (2006.01)
*C22C 19/05* (2006.01)
*G16C 20/50* (2019.01)

(52) U.S. Cl.
CPC ............ *G16C 20/30* (2019.02); *C22C 19/007* (2013.01); *C22C 19/056* (2013.01); *C22C 19/057* (2013.01); *G16C 20/50* (2019.02)

(58) Field of Classification Search
None
See application file for complete search history.

(56) References Cited

U.S. PATENT DOCUMENTS

| | | | |
|---|---|---|---|
| 2006/0054251 A1 | 3/2006 | Yokokawa et al. | 148/508 |
| 2006/0074594 A1 | 4/2006 | Ceder et al. | 702/182 |
| 2009/0035170 A1* | 2/2009 | Nakajima | B22D 11/0611 420/83 |
| 2014/0236548 A1 | 8/2014 | Conduit et al. | 703/2 |

FOREIGN PATENT DOCUMENTS

| | | |
|---|---|---|
| EP | 0633534 | 1/1995 |
| EP | 2778990 | 9/2014 |
| GB | 2241358 | 8/1991 |
| JP | 09-259156 | 10/1997 |
| WO | WO 2015/054657 | 4/2015 |

OTHER PUBLICATIONS

Curtarolo et al., "The High-Throughput Highway to Computational Materials Design," *Nature Materials*, 2013; 12(3): 191-201.
International Preliminary Report on Patentability issued for Application No. PCT/GB2016/050810, dated Oct. 3, 2017.
International Search Report and Written Opinion issued in Application No. PCT/GB2016/050810.
Reed et al., "Alloys-by-Design: Application to Nickel-Based Single Crystal Superalloys," *Acta Materialia*, 2009; 57(19): 5898-5913.
Reith et al., "Towards an ab initio modelling of phase diagram: Cluster Expansion and vibrational free energies," URL: <http://www.vsc.ac.at/fileadmin/user_upload/vsc/reports/UNI-p70034-p70134-Podloucky-Report.pdf>. The Reith et al. reference does not include a publication date. However, this reference was retrievable from the provided hyperlink prior to the priority date of the present application.
Search Report issued in United Kingdom Patent Application No. 1505652.6, dated Sep. 17, 2015.

* cited by examiner

*Primary Examiner* — Russell S Negin
(74) *Attorney, Agent, or Firm* — Norton Rose Fulbright US LLP

(57) ABSTRACT

A computer assisted method of designing a designed alloy composition comprising a plurality of elements, the method comprising the steps of: populating a multi-dimensional alloy space with a plurality of candidate alloy compositions, the plurality of candidate alloy compositions including for each of the plurality of elements at least three candidate alloy compositions with different amounts of the respective element to each other; performing at least one test on each individual one of the plurality of candidate alloy compositions until each of the individual ones of the plurality of candidate alloy compositions fails a test or has passed all tests; outputting the designed alloy composition based on one or more of the individual ones of the plurality of candidate alloy compositions which have passed all tests, wherein the at least one test includes at least: a phase equilibrium test in which predicted phase equilibrium is determined as a function of elemental composition of the individual one of the plurality of candidate alloy compositions; and at least one merit index test in which a predicted property of the individual one of the plurality of candidate alloy compositions is predicted as a function of the elemental composition of the individual one of the plurality of candidate alloy compositions and failing the individual one of the plurality candidate alloy compositions if the predicted property does not meet a desired predicted property.

15 Claims, 12 Drawing Sheets

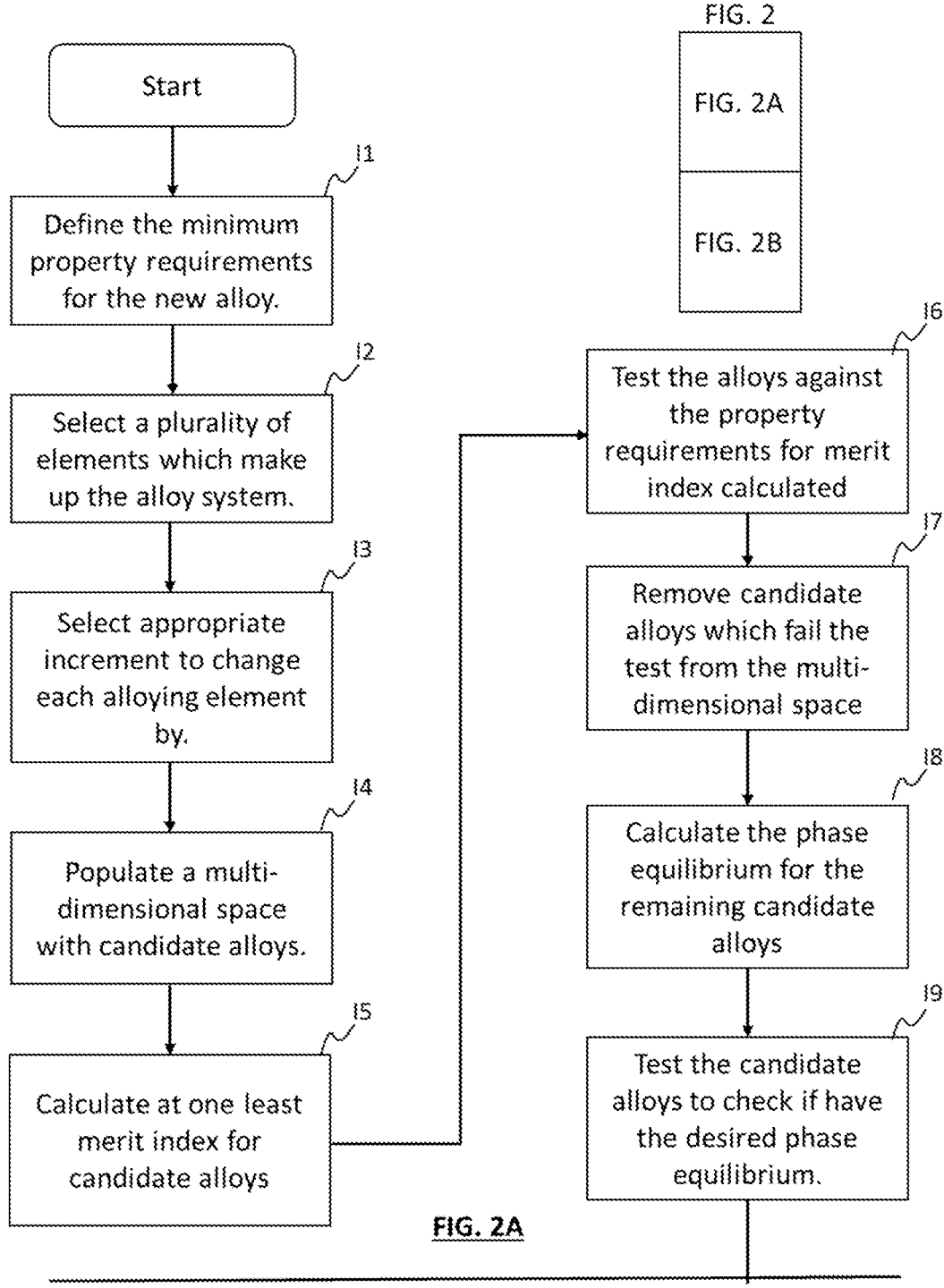

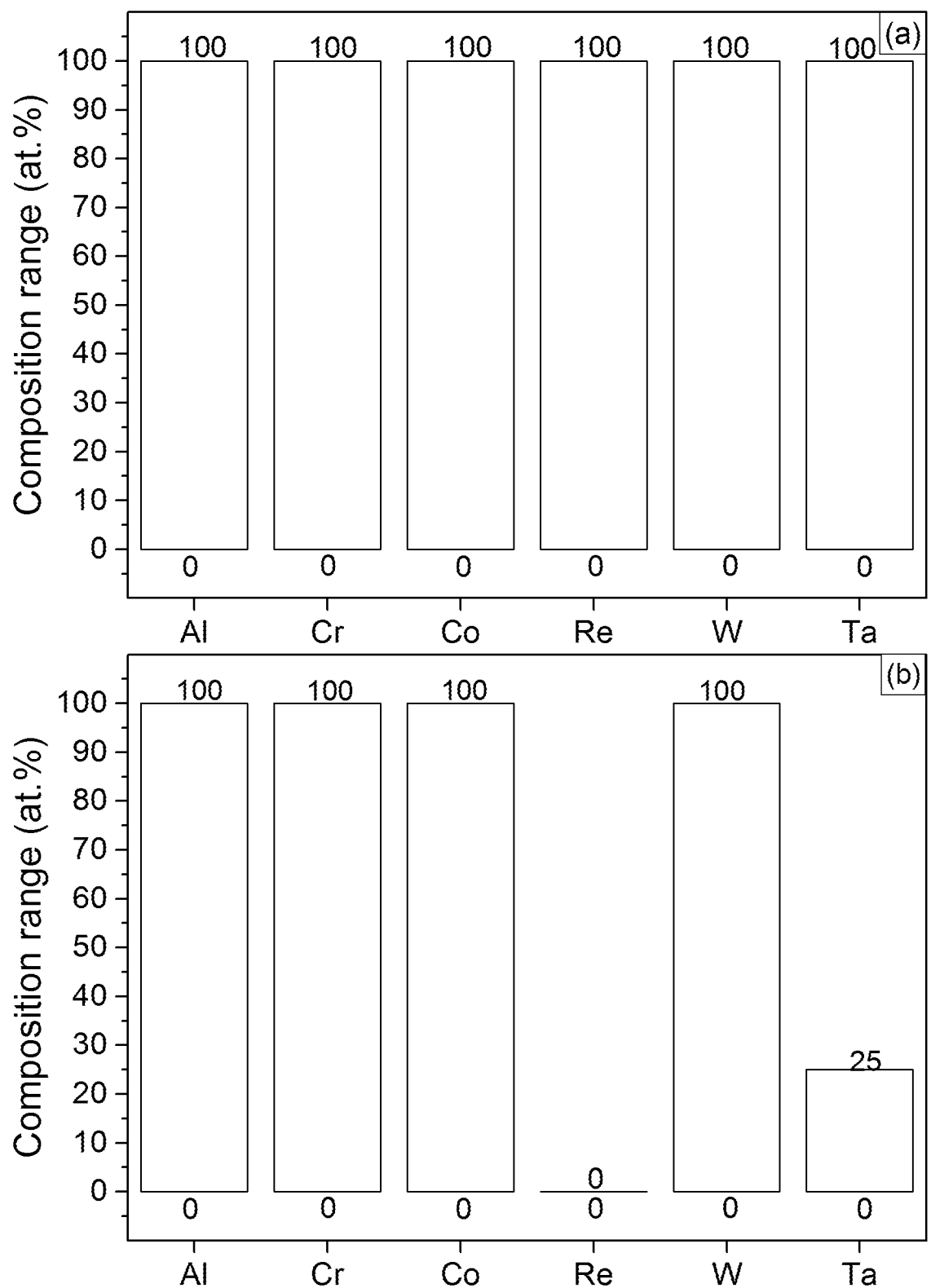
Figure 3 (a) & (b)

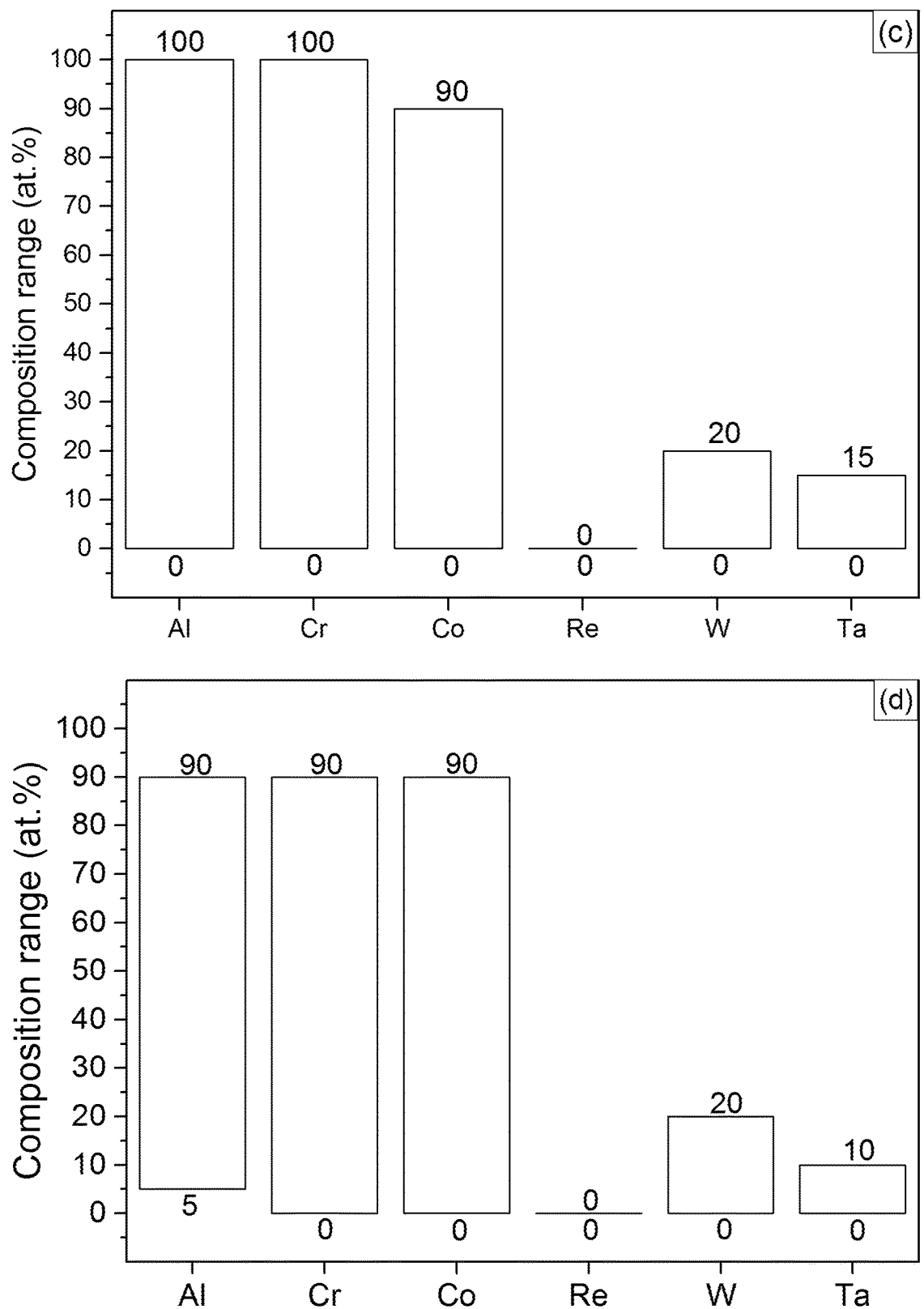
Figure 3 (c) & (d)

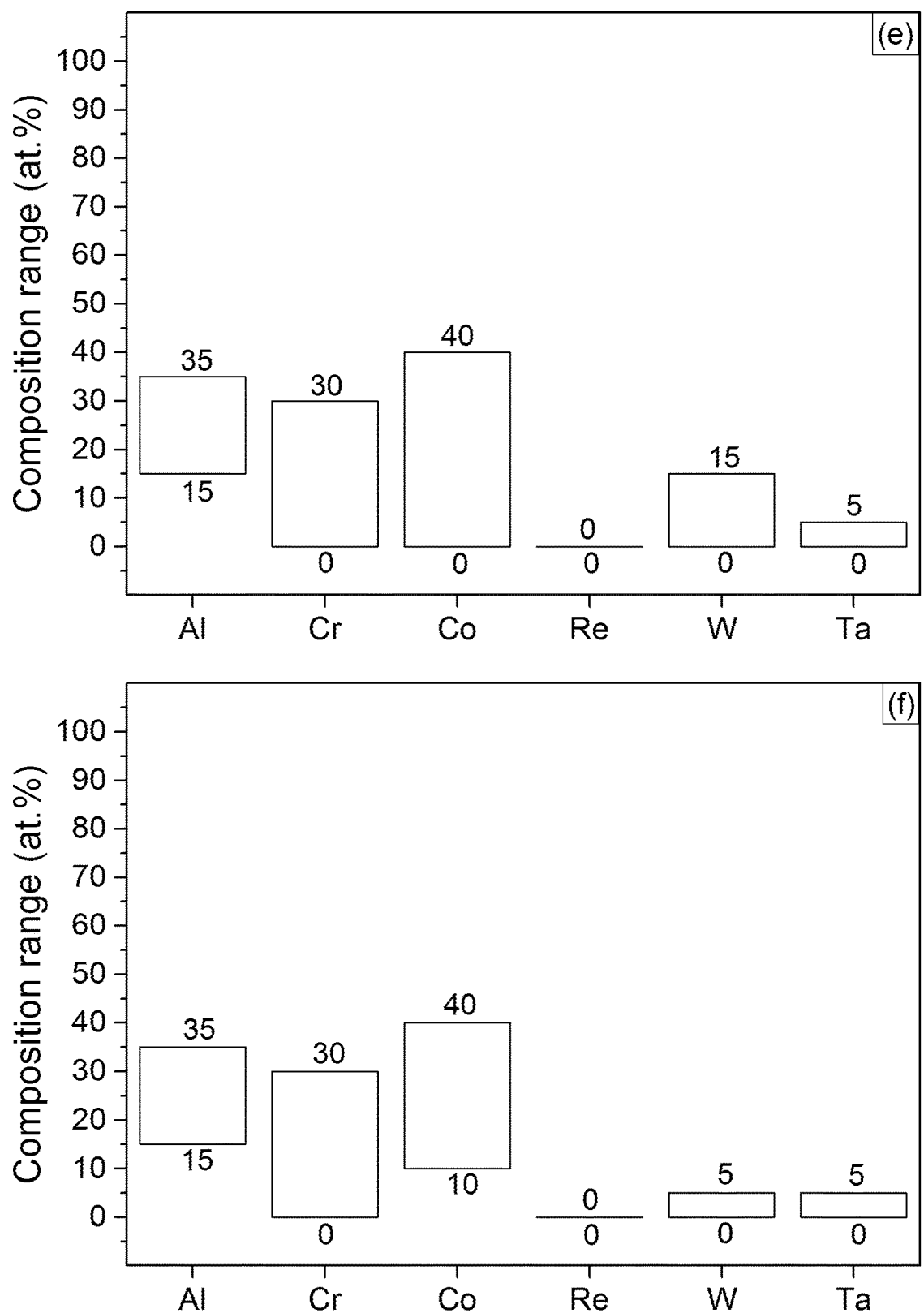
*Figure 3 (e) & (f)*

Figure 4:
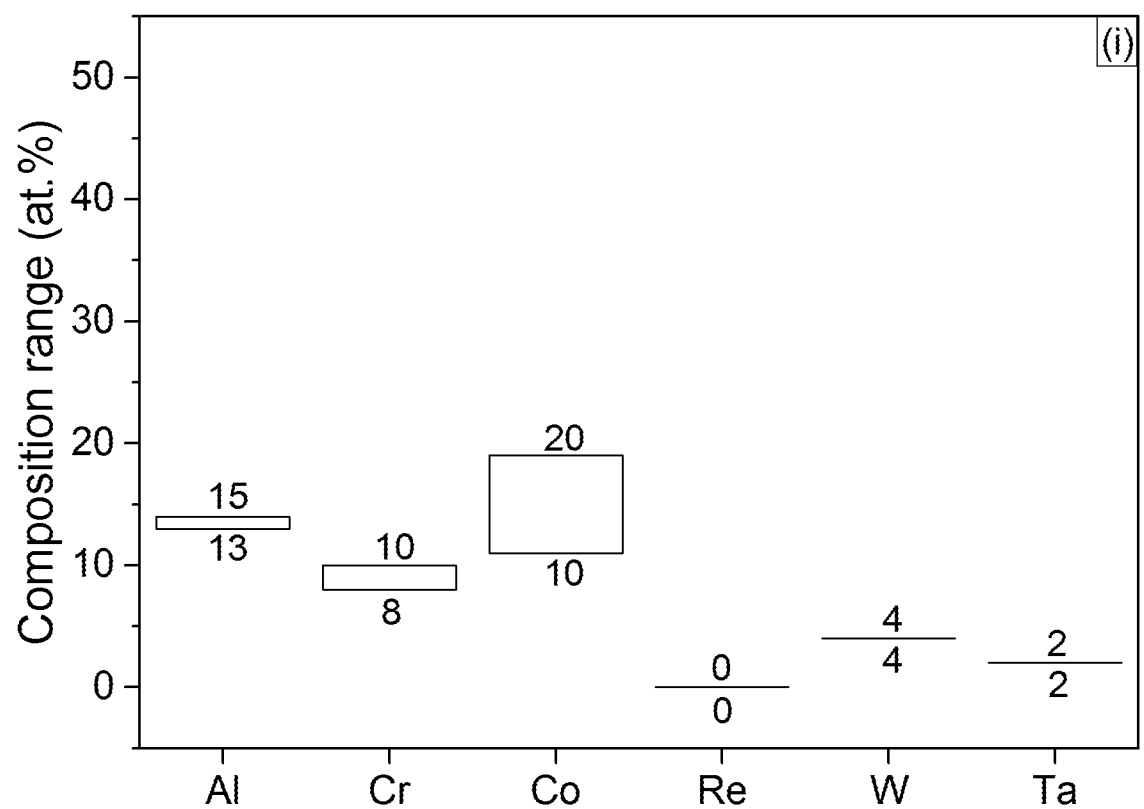

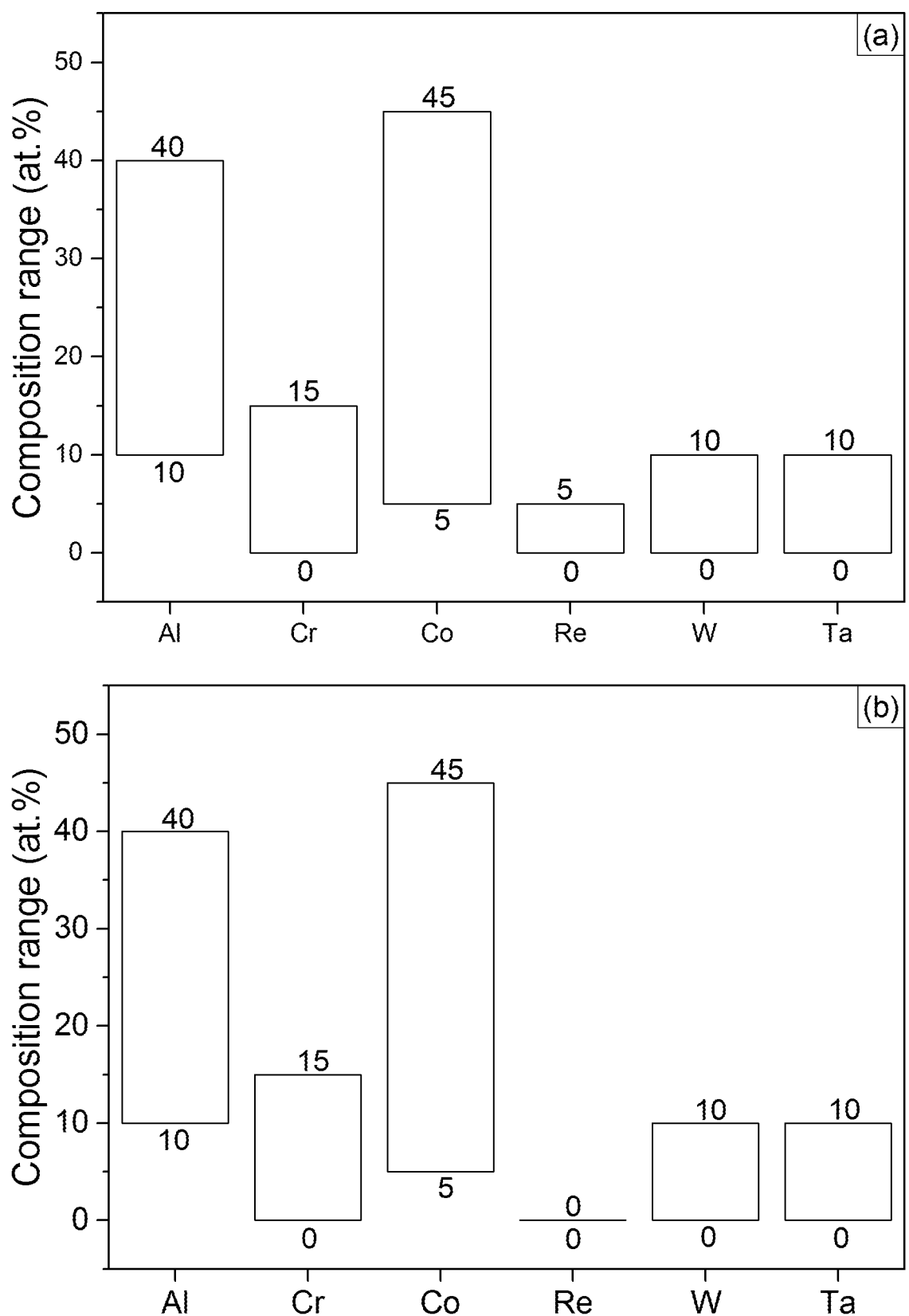
Figure 4 (a) & (b)

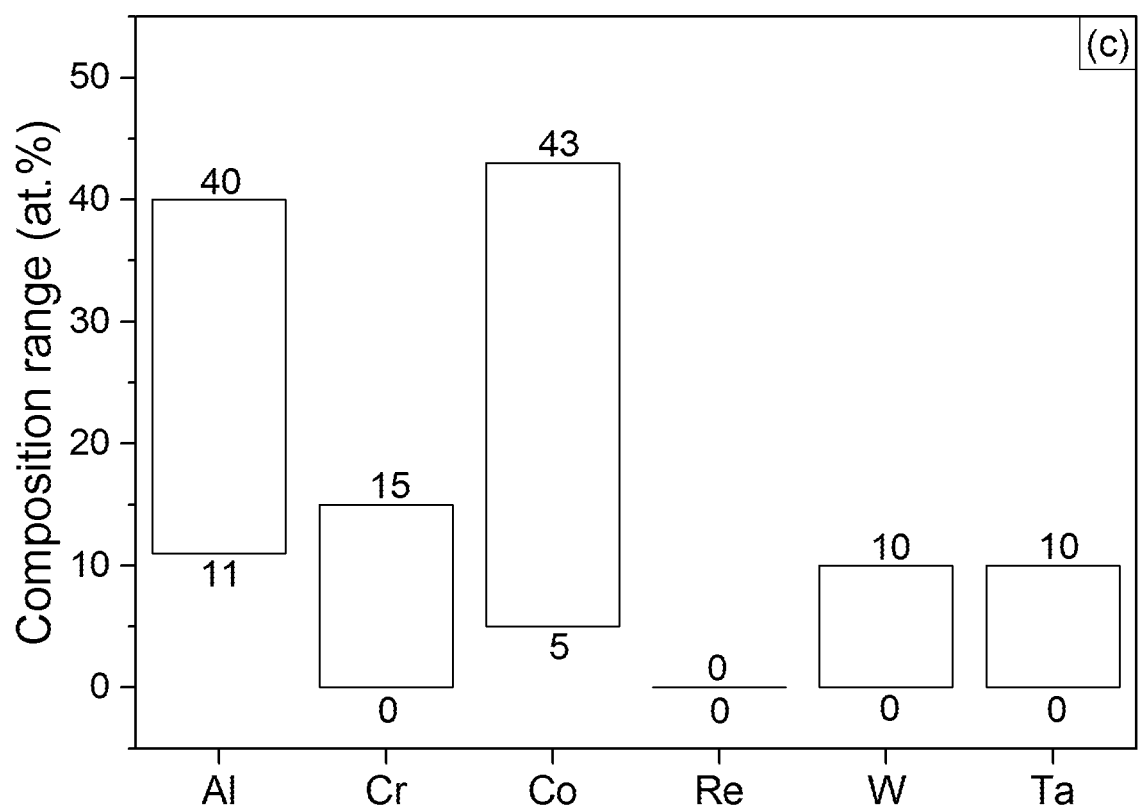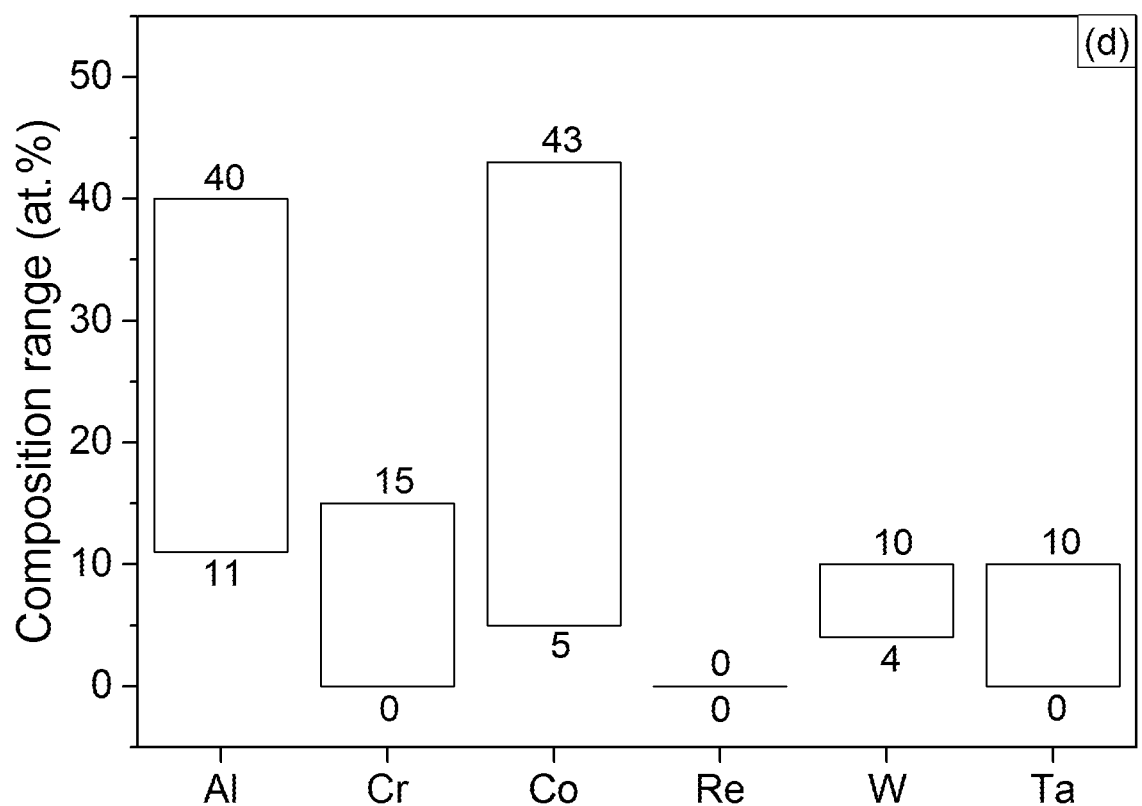
*Figure 4 (c) & (d)*

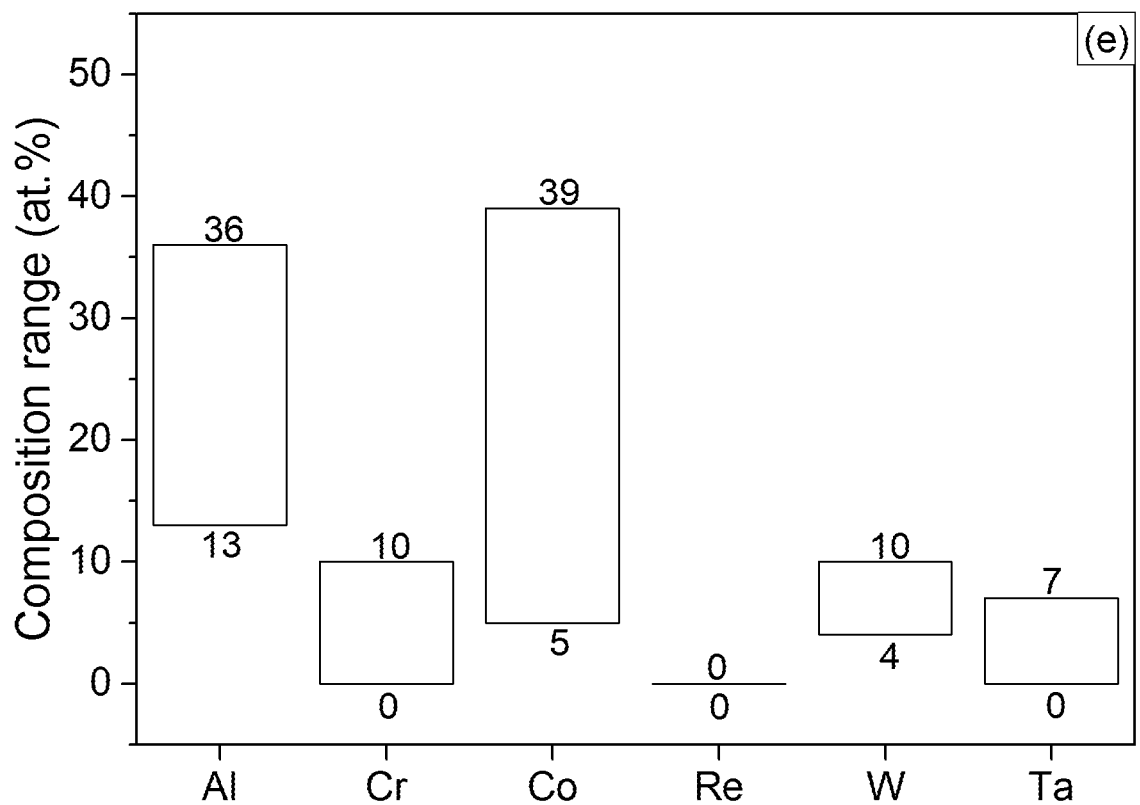
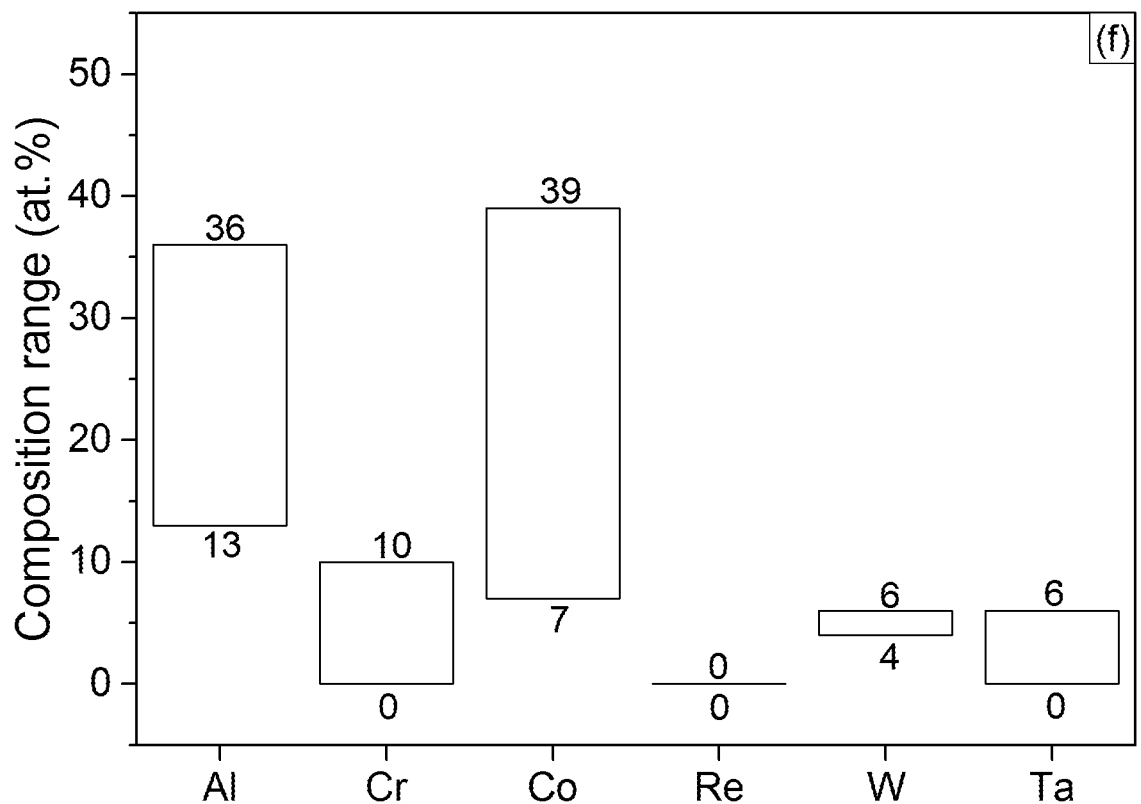
*Figure 4 (e) & (f)*

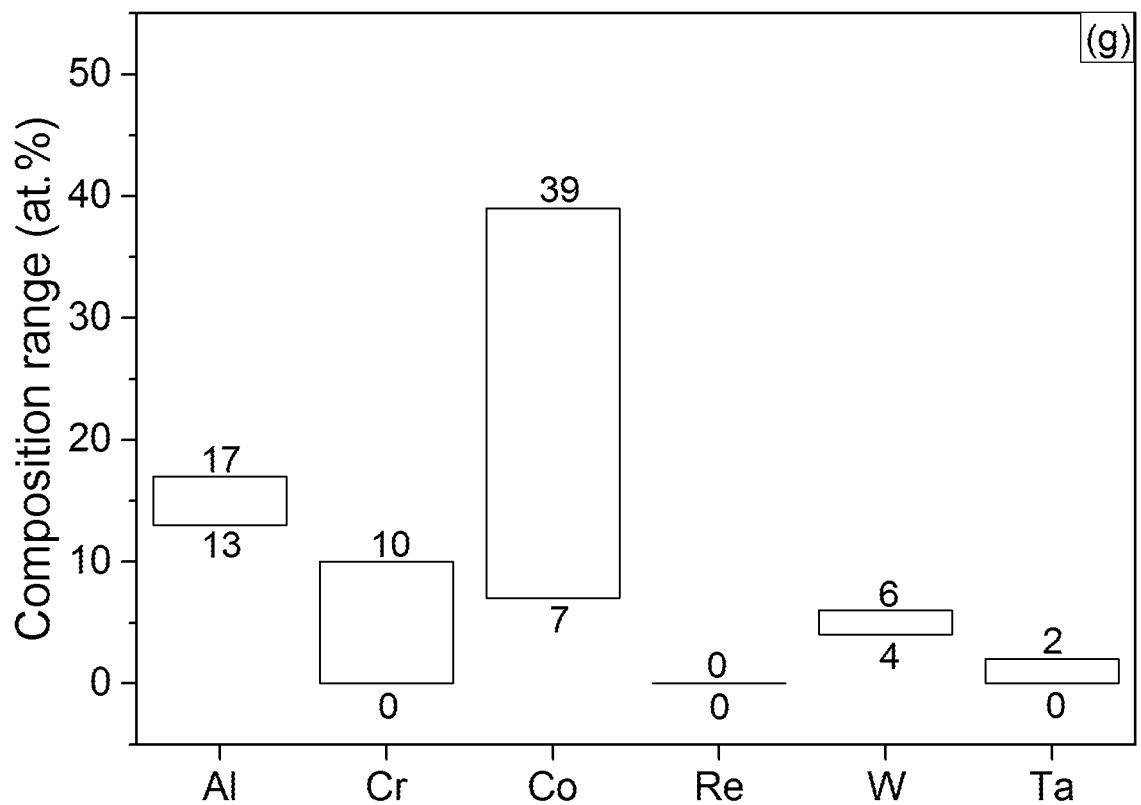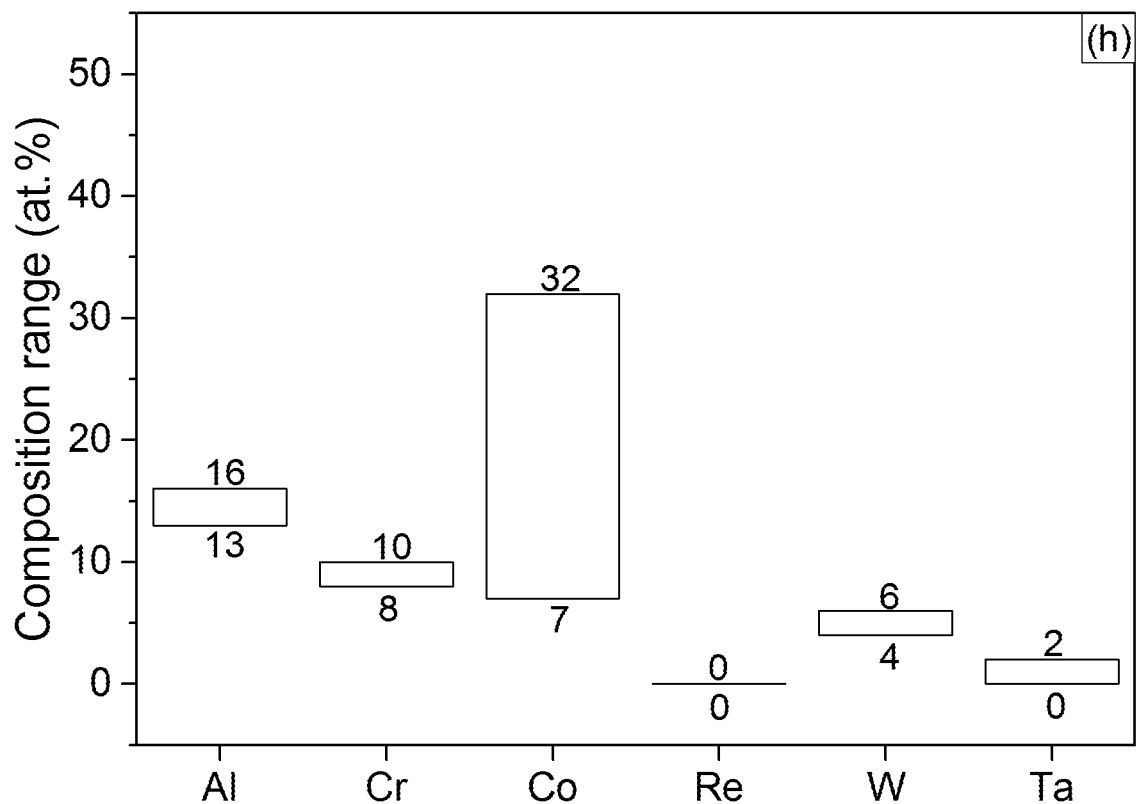
Figure 4 (g) & (h)

METHOD FOR DESIGNING ALLOYS

CROSS-REFERENCED TO RELATED APPLICATION

This application is a national phase application under 35 U.S.C. § 371 of International Patent Application No. PCT/GB2016/050810 filed Mar. 23, 2016, which claims priority to U.K. Patent Application No. GB1505652.6, filed Apr. 1, 2015. The entire contents of the referenced applications are incorporated herein by reference.

The present invention relates to a computer assisted method for designing an alloy composition. The approach allows for a multi-dimensional alloy space comprised of a plurality of elements to be searched for an alloy composition with a desired or optimal balance of properties. This method represents a paradigm shift from conventional empirically based alloy development.

BACKGROUND

Metallic alloys are widely used to produce structural components for engineering applications because of their ability to withstand substantial mechanical and thermal loads. The development of different engineering alloys is often inextricably linked with the emergence of new technologies. For example, the development of aluminium alloys was a key enabler for the introduction of aircraft, or the discovery of the nickel-based superalloys made gas turbine engine technology possible. The properties of alloys used to produce such structural components—for example, tensile strength, creep resistance or corrosion resistance—may often be the limiting factor in the overall performance of a particular engineered device. Thus, optimising the composition of an alloy to improve the overall balance of properties is critical to the development of improved technology.

However, the balance of desirable properties in engineering alloys is largely dependent upon their chemical complexity, with structural alloys possibly containing 10 or more different alloying elements. The conventional methodologies employed when developing new alloy compositions are slow, labour intensive and costly. The development process has been—and still is—predominantly reliant upon trial-and-error based approaches backed up by empirical property testing. Based upon the enormous number of possible permutations which exist within an alloy system containing a plurality of elements it is improbable that optimal compositions could be discovered using empirically based design methods.

Figure 1:
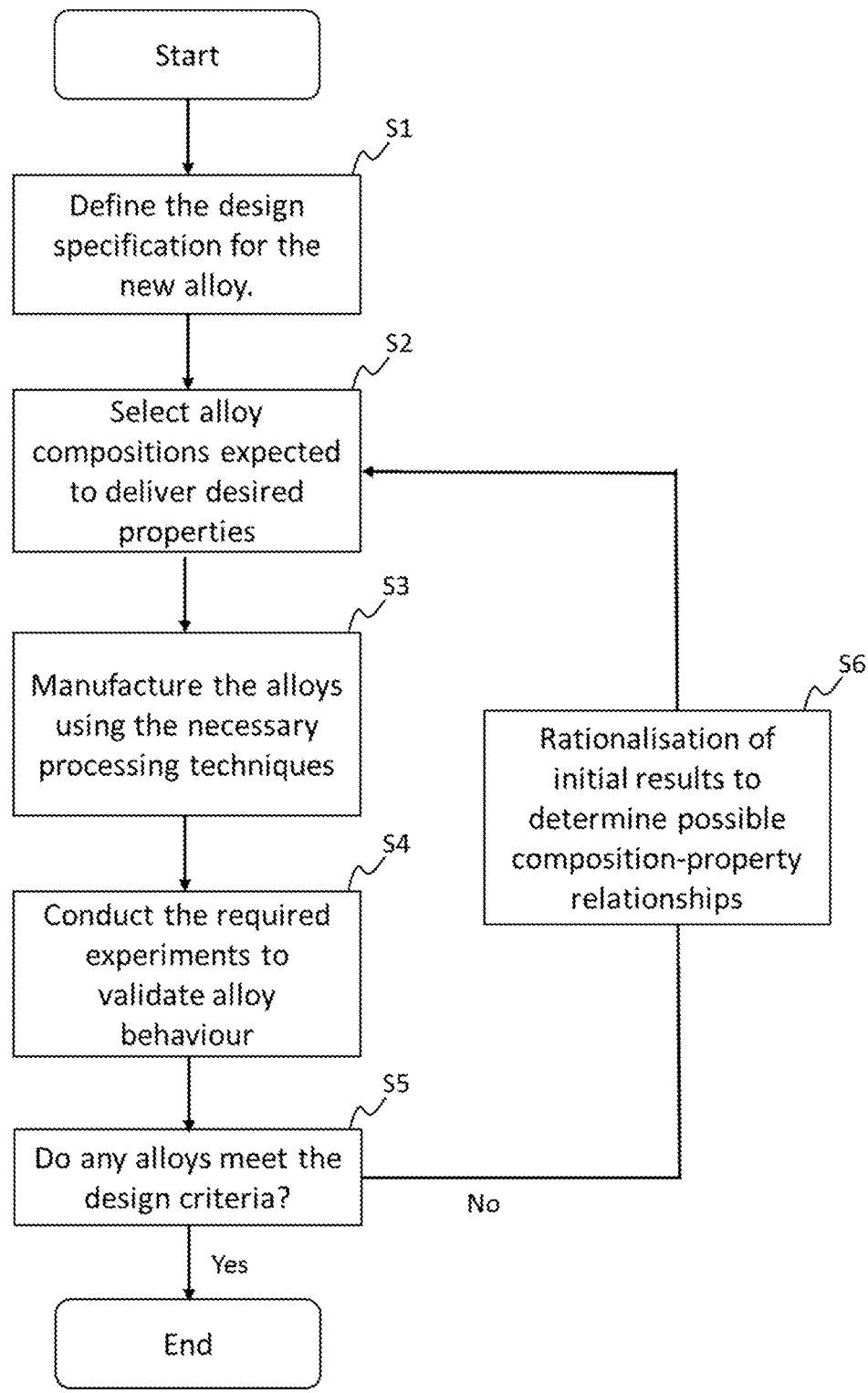

An overview of the typical process followed in conventional alloy design is presented in FIG. 1, in FIG. 1 S represents a step.

The conventional approach to alloy development normally begins by defining the properties required for the new material (S1). A number of trial compositions are defined (S2), these alloys are anticipated to have the desired properties. The selection of these alloy compositions is somewhat arbitrary and is reliant upon experts with a detailed understanding of the alloy system of interest. Typically, the number of alloys studied will be limited to less than 100 different compositions. However, due to many different factors—for example, time and cost—the number alloys produced may be considerably less than this.

As the number of alloys produced is limited, the compositions selected may not differ greatly. Also, in practice the compositions of new trial alloys are often derived from a previously successful alloy or group of alloys. Thus, a weakness in the traditional approach exists as preconception or subjectivity is inherent within the composition of the trial alloys selected. Moreover, the limited number of compositions studied results in a compositional space/range which is narrow.

Following the selection of the individual trial compositions it is necessary to manufacture each alloy (S3). At the point which the trial compositions are manufactured no information is available to quantify the properties of the alloys, so it is unknown if any composition will meet required design specification. Therefore a risk exists as there may be a significant degree of uncertainty regarding the likelihood of trial compositions being amenable to the processing methodology used for the manufacture of the trial compositions. Production of these trial compositions may have significant lead-times, particularly when the use of specialist processing techniques are required. Hence, the financial investment and time-scales associated with the production of the trial alloys has a high degree of associated risk.

Once the trial alloys have been manufactured, a series of experiments are required to characterise the properties of each material (S4). It is possible that significant volumes of experimental testing may be required. Furthermore, experiments for design critical properties may have to be conducted over extensive time periods e.g. creep testing, assessment of microstructural stability or corrosion tests. Often during the development process only limited quantities of the trial alloys may be available. This may result in a number of issues. For example, it may not be possible to assess all the design relevant properties for the material. Also, it may not be possible to produce enough experimental data to be statistically representative of actual alloy behaviour, for example fatigue properties.

After the experimental assessment of each trial alloy is completed it may be possible to select a composition with best balance of material properties for deployment (S5). This may not necessarily mean that all material properties have been attained. Furthermore, it may be possible that alloy composition with a better balance of properties exists for the intended application but was not discovered due to the limited compositional space searched and the limited number of trial compositions studied.

If none of the trial compositions meets the minimum property requirements, statistical methods may be used to correlate the effect of alloy composition with material properties (S6). These statistical methods—for example, regression analysis—are limited as it is improbable that the relationship between composition and performance is adequately described. Due to the number of alloying elements and the physics which govern the materials behaviour, complex non-linear relationships often exist between composition and properties. It is unlikely that a dataset of experimental results will be statically representative to describe variation within a multi-dimensional composition space. Furthermore, introduction of new alloying elements or extrapolation outside the original design space decreases the probability that correlations made between composition and properties are sufficiently accurate to allow for optimisation.

The composition-property relationships derived from statistical analysis may be used to determine new compositions expected to have improved properties. Selection of subsequent trial compositions requires a further iteration of the make-test process described previously, significantly impacting upon the cost and time-scales associated with discovery of the best possible alloy. These subsequent iterations of the make-test process may result in an alloy with a suitable balance of properties. Although due to the ambiguous—or blind—nature of the design process it is not guaranteed that an alloy with the property specification required is even physically possible.

The problems associated with conventional alloy design methods described above—mainly cost and time-scale—have obstructed the possibility for rapid and efficient design of alloys optimised for the specific applications. Previously, this has resulted in the use of pre-existing alloys not optimal for the intended application, potentially to the detriment of the particular engineering device. However, growing demand for improved efficiency in applications such as transportation or energy production has resulted in a definite need for better harmonisation between component design and alloy design.

Thus, improving the methodology for designing alloys is a major challenge within the field of metallurgy. An objective of this present invention is to provide a method which allows alloy compositions to be designed using a computer assisted method, eliminating the need for empirical development and solving the above mentioned problems.

The present invention provides a computer assisted method of designing a designed alloy composition comprising a plurality of elements, the method comprising the steps of: populating a multi-dimensional alloy space with a plurality of candidate alloy compositions, the plurality of candidate alloy compositions including for each of the plurality of elements at least three candidate alloy compositions with different amounts of the respective element to each other; performing at least one test on each individual one of the plurality of candidate alloy compositions until each of the individual ones of the plurality of candidate alloy compositions fails a test or has passed all tests; outputting the designed alloy composition based on one or more of the individual ones of the plurality of candidate alloy compositions which have passed all tests, wherein the at least one test includes at least: a phase equilibrium test in which predicted phase equilibrium is determined as a function of elemental composition of the individual one of the plurality of candidate alloy compositions; and at least one merit index test in which a predicted property of the individual one of the plurality of candidate alloy compositions is predicted as a function of the elemental composition of the individual one of the plurality of candidate alloy compositions and failing the individual one of the plurality candidate alloy compositions if the predicted property does not meet a desired predicted property.

Thus, a method for designing a new alloy composition is provided in which the need for empirical development is eliminated.

In an embodiment of the computer assisted method in the performing step the plurality of tests are performed one after the other in an order starting with the least computationally intensive test. In this way the computational efficiency of the method is improved as tests need not be performed on candidate alloy compositions if those candidate alloy compositions have already been excluded on the basis of a less computationally intensive test.

In an embodiment of the computer assisted method in the performing step at least one merit index test is performed after the phase equilibrium test and is a function of an aspect of the predicted phase equilibrium for the respective individual one of the plurality of candidate alloy compositions. In this way the need for performing the same or similar phase equilibrium calculations multiple times is avoided.

In an embodiment of the computer assisted method the phase equilibrium test further comprises failing the individual one of the plurality of candidate alloy compositions if the predicted phase equilibrium does not meet a desired predicted phase equilibrium. Thus, it is possible to use the method to design an alloy with certain desired microstructural properties as well as certain predicted properties according to the at least one merit index test.

An embodiment of the computer assisted method further comprises receiving an input indicative of at least one temperature and/or pressure at which the predicted phase equilibrium is determined and/or an input indicative of whether stable equilibrium or meta-stable equilibrium phase fractions are to be calculated. In this way the operating requirements of the designed alloy composition can be reflected in the computer assisted method of designing the designed alloy composition.

An embodiment of the computer assisted method further comprises receiving an input relating to which elements make up the plurality of elements and/or maximum and/or minimum content of at least one of the elements of the plurality of elements, thereby to define the limits of the multi-dimensional alloy space. In this way the computational intensity of the method can be reduced if it is known, for example, that certain alloy compositions will not meet the at least one desired predicted property such that the at least one test need not be performed on candidate alloy compositions which are known would fail the at least one test.

An embodiment of the computer assisted method further comprises receiving, for at least one element of the plurality of elements, an input relating to a magnitude of a difference in content of that element between adjacent candidate alloy compositions. Thus, it is possible to increase or decrease the number of candidate alloy compositions which populate the multi-dimensional alloy space to an appropriate level for the stage of the design.

An embodiment of the computer assisted method further comprises the step of carrying out the populating step on a new multi-dimensional alloy space to define a new plurality of candidate alloy compositions and carrying out the performing and outputting steps on the new plurality of candidate alloy compositions. In this way the computational efficiency of the method is increased by redefining the multi-dimensional alloy space to an appropriate extent before proceeding to the next test.

In an embodiment of the computer assisted method the new multi-dimensional alloy space is a subset of the multi-dimensional alloy space and is based on the designed alloy composition.

In an embodiment of the computer assisted method the carrying out further includes receiving an input relating to maximum and/or minimum content of at least one of the elements of the plurality of elements thereby to define the limits of the new multi-dimensional alloy space as a subset of the multi-dimensional alloy.

An embodiment of the computer assisted method further comprises: receiving, for at least one element of the plurality of elements, an input indicative of a modified magnitude of a difference in content of that element between adjacent candidate alloy compositions of the new multi-dimensional alloy space. Thus, it is possible to increase the computational efficiency of the method by reducing the size of the multi-dimensional alloy space prior to reducing the magnitude of a difference in content of an element between adjacent candidate alloy compositions whilst still performing the tests at high resolution.

An embodiment of the computer assisted method further comprises: receiving an input indicative of a modification to the desired predicted property of at least one of the at least one merit index tests and/or receiving an input indicative of a modification to the desired phase equilibrium. Thus, it is possible to modify the desired predicted property for example if the multi-dimensional alloy space becomes too small (or none of the candidate alloy compositions meet the desired predicted property) or to decrease the multi-dimensional alloy space and achieve a better desired predicted property.

Although the invention has been described as applied to nickel based superalloy systems, the same principles can be applied to other alloy systems (e.g. steels, titanium alloys, aluminium alloys etc.). In other alloy systems some of the merit index tests described herein will be applicable or adaptable, as will the phase equilibrium test. Additionally other merit index tests could be developed for the other alloys systems, or indeed for nickel based superalloy systems. However, the principles of the present invention will apply too any alloy system in terms of providing a method for designing an alloy which avoids large experimental matrices and is computationally efficient.

Figure 2B:
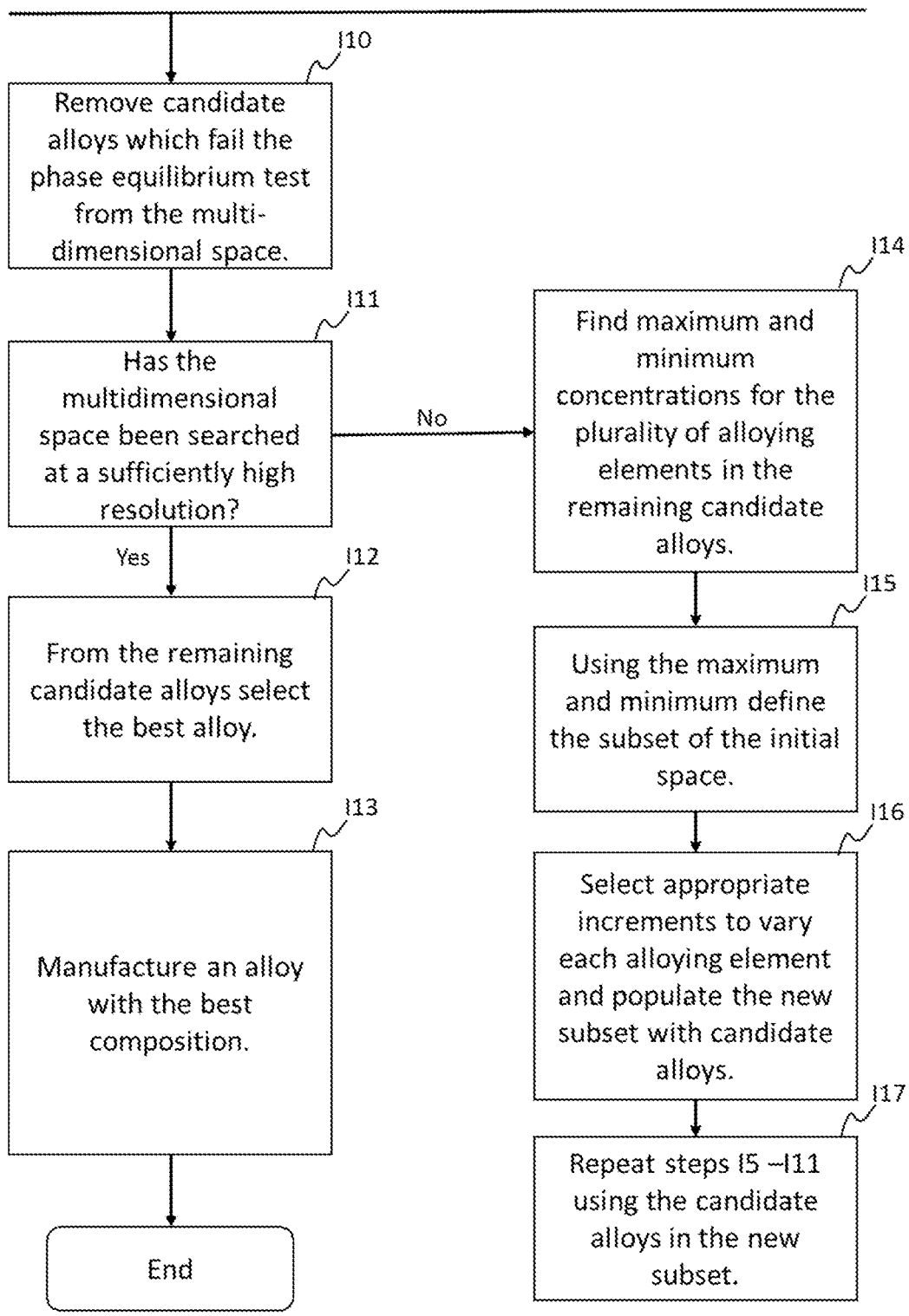
Figure 5:
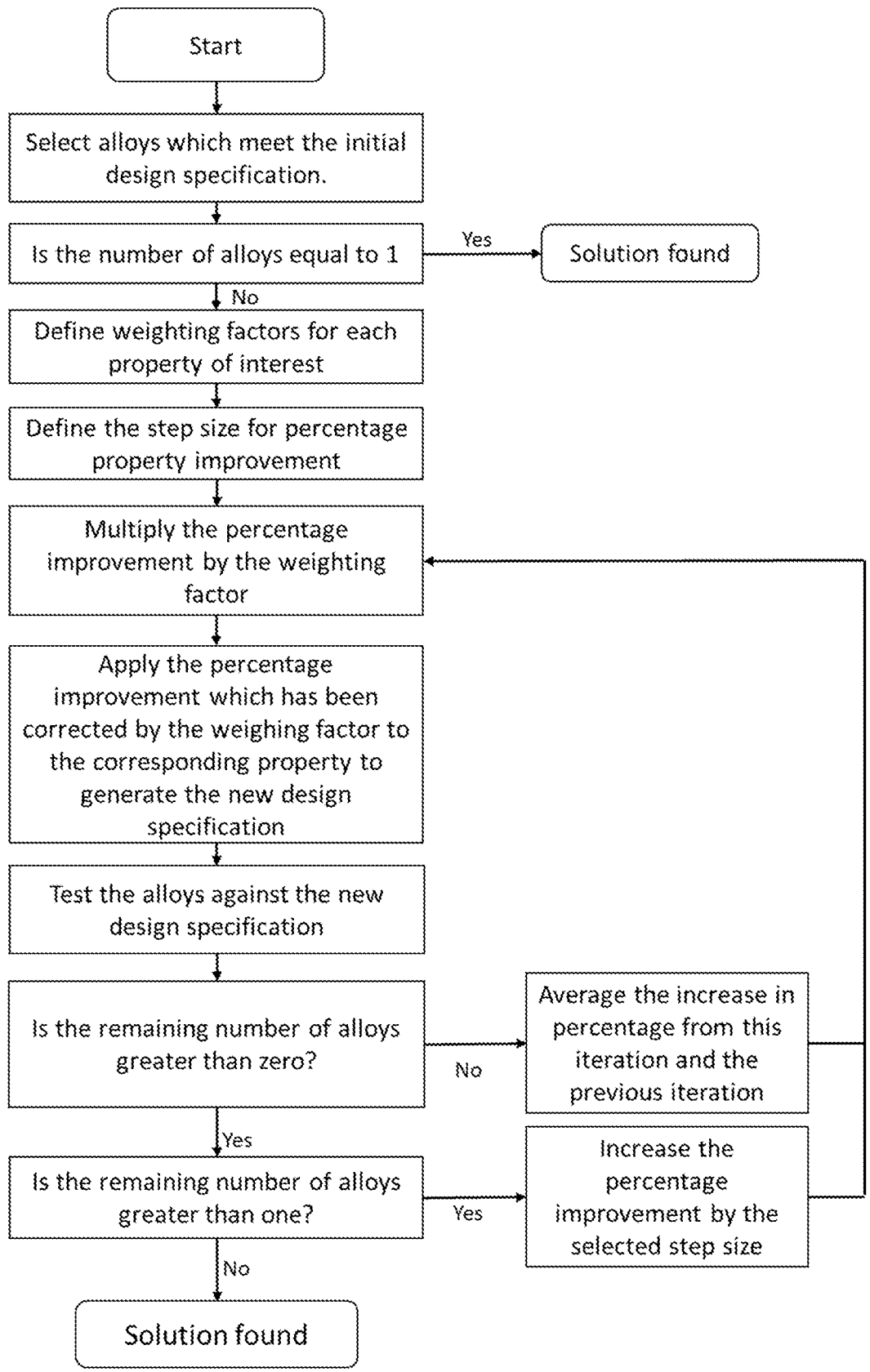

The present invention will be described by way of example only with reference to the accompanying Figures in which:

FIG. 1 is a flow chart illustrating the conventional empirically based approach used for discovery of alloy compositions;

FIGS. 2 (a) and (b) are a flow chart illustrating the steps involved in implementing the computational alloy design methodology;

FIGS. 3 (a)-(f) show the evolution of a multi-dimensional alloy space using an interval of 5 atomic %. In (a) the initial design space is depicted before testing, after which tests for (b) cost, (c) density, (d) creep resistance, (e) γ' proportion, and (f) proportion of TCP phases are applied;

FIGS. 4 (a)-(i) show the evolution of the multi-dimensional alloy space using an interval of 1 atomic %. In (a) the initial multi-dimensional alloy space is depicted before testing, after which tests for (b) cost, (c) density, (d) creep resistance, (e) γ' proportion, (f) proportion of TCP phases, (g) heat treatment window, (h) oxidation resistance, and (i) anti-phase boundary energy are applied; and FIG. 5 is a flow chart outlining the process used for selection of an optimum alloy composition when selecting the composition of the new second generation single crystal nickel based super alloy.

DISCLOSURE OF THE INVENTION

The understanding of the physical mechanisms which govern the behaviour of metallic alloys has progressed over the past century. This knowledge has led to the formulation of models—across a variety of length scales e.g. atomic-scale, micro-scale, meso-scale—that can accurately predict a range of different material properties. Furthermore, the development of low cost, high powered computational facilities has made it economical to conduct large volumes of complex calculations.

A computer assisted method used for the design of a new designed alloy composition is described here. This approach utilises a framework of computational materials models—with each model referred to as a test—to estimate design relevant properties across the entirety of a multi-dimensional alloy space which is comprised from a plurality of elements. The tests include at least one merit index test. In a merit index test a computational materials model is used to predict a property as a function of the elemental composition. The tests also include a phase equilibrium test in which a predicted phase equilibrium is determined as a function of elemental composition. The tests may be performed in any order, though an order of increasing computational intensity is preferred. The multi-dimensional alloy space is reduced in size after each test or after a group of tests such that only candidate alloy compositions which have passed all tests performed up to that time remain in the multi-dimensional alloy space. Thus, the multi-dimensional alloy space is reduced in size. After all of the predetermined tests have been performed the computer assisted method outputs the designed alloy composition based on one or more candidate alloy compositions from the original multi-dimensional alloy space which have passed all tests. Thus, all possible permutations of alloy compositions for a given plurality of elements can be considered in that at least one test will have been performed on all possible permeations of alloy compositions. In principle, this alloy design tool allows for the isolation of alloy compositions optimised to best satisfy a specified set of design constraints.

An overview of the typical process followed in the method of the present invention is presented in FIG. 2. In FIG. 2 I represents a step. The order of the steps in FIG. 2 is a preferred order but the invention can be performed in a different order. The method may return to step I3 after one or more tests or phase equilibrium calculations have been performed and the method may omit one or more steps if they are not required, particularly during repetition of steps of the method.

The process may begin by receiving an input indicative of one or more desired predicted properties i.e. defining minimum requirements for one or a number of properties for the new alloy (I1). Thus, maximal and/or minimum limits for one or more merit indices may be defined, these maximal and/or minimum requirements act as the boundary conditions to the design problem. In some instances it may be possible that merit indices are calculated for known alloy compositions in order appropriately to determine the maximal and or minimal limits for a given merit index. The process may also receive an input indicative of the desired phase equilibrium.

In the next step of the process an input is received relating to which elements make-up the plurality of elements of the multi-dimensional alloy space i.e. defining an alloy system to search for the new alloy composition (I2). This involves selection of the plurality of elements which define the alloy system of interest. The method can consider additions of each individual element through the entirety of its range i.e. between 0 and 100 percent. The default will be to consider each individual element through the entirety of its range (i.e. 0-100 percent). However, the method can also receive an input relating to maximum and/or minimum content of at least one of the elements of the plurality of elements. For example it may be known that content of say tungsten for a super alloy need only be considered between zero and 40%. Defining maximum and minimum contents can save on computational time. Thus, in step I2, the limits of the multi-dimensional alloy space are defined.

The order of steps I1 and I2 may be reversed.

The next step involves populating the multi-dimensional alloy space comprised of the plurality of selected elements with a plurality of candidate alloy compositions (I3-I4). This is achieved by selecting suitable increments by which each elemental addition is varied (I3). This increment is selected such that at least three, preferably at least five or at least ten candidate alloy compositions with different amounts of the respective elements to each other. In this way, the effect of each element can be tested. The increments may be selected automatically by the computer. Additionally or alternatively, the method may receive, for at least one element of the plurality of elements, an input relating to a magnitude of a difference in content of that element between adjacent candidate alloy compositions. Thus, a user may define the increment for a given element to be different (or the same) to other elements. This may be advantageous, for example, where it is known or suspected that the desired property will be particularly sensitive to a certain element. For that certain element it might be advantageous to select a lower increment than for other alloys.

In an embodiment of the method it may be that increments are made sufficiently large such that the plurality of candidate alloys are limited to a number for which it is not too computationally expensive to calculate one or more of the merit indices. In another variation of the method it may be that the minimal increment size by which an individual alloying element is varied is automatically selected to be larger than or substantially equal to the tightest possible tolerance achievable by the manufacturing process used to produce the alloy composition selected.

The next step involves using the increment size determined for each alloying element in step I3 to populate the multi-dimensional alloy space with a plurality of candidate alloy compositions (I4), the plurality of candidate alloy compositions including for each of the plurality of elements at least three candidate alloy compositions with different amounts of the respective element to each other. In this way the whole of the multi-dimensional alloy space is populated with candidate alloy compositions and all possible permutations are covered.

The next step involves performing at least one test on each individual candidate alloy composition (I5-I7). To perform the test, one or more merit index values are calculated as a function of the elemental composition of each candidate alloy composition (I5). Each merit index calculated for a given candidate alloy composition can be tested against the maximal and/or minimal limit of the respective merit index defined prior to the calculation (I6). If the merit index calculated for a given candidate alloy composition does not meet the desired property requirement then the candidate alloy composition in question fails that test and is removed from the multi-dimensional alloy space (I7).

In an embodiment all candidate alloy compositions are subjected to a first merit index test. Any individual ones of the plurality of candidate compositions which are not calculated to have a predicted property which meets the desired predicted property are failed. Subsequent merit index tests or phase equilibrium tests are not performed on that candidate alloy composition. One or more merit index tests may be performed one after the other. Additionally or alternatively, after a particular merit index test has been performed, the method may return to step I1 where the multi-dimensional space is re-defined based on the candidate alloy compositions which have passed the merit index test(s). The new multi-dimensional alloy space is re-populated to define a new plurality of candidate alloy compositions either using the previously defined increments or using newly defined increments. Subsequent tests are carried out on the new plurality of candidate alloy compositions.

After the first test the method may output a designed alloy composition based on one or more of the individual ones of the plurality of candidate alloy compositions which have passed the test(s). This output may be used to define the new multi-dimensional alloy space. The new multi-dimensional alloy space is a subset of the (original or previous) multi-dimensional alloy space. The new multi-dimensional alloy space may be defined by receiving an input relating to maximum and/or minimum content of at least one of the elements of the plurality of elements, thereby to define the limits of the new multi-dimensional alloy space as a subset of the multi-dimensional alloy. In this way user input, based on the output designed alloy composition may be made. User input may also be received defining a new difference in content for one or more selected elements between adjacent candidate alloy compositions as described above in relation to step I3. Additionally or alternatively an input may be received indicative of a modification to the desired predicted property of at least one of the at least one merit index tests and/or receiving an input indicative of a modification to a desired phase equilibrium (equivalent to step I1).

In an embodiment of the method, calculation of the different merit indices may involve conducting the calculations for all the candidate alloy compositions covering the entire population of the multi-dimensional composition space in order of computational intensity, such that the least computationally intense calculation is completed first. As each merit index is calculated for all candidate alloy compositions in the multi-dimensional space, alloys will be tested. Candidate alloy compositions which fail the test (i.e. the calculated merit index does not meet the maximal and/or minimal design requirement) will be removed from the multi-dimensional alloy space. By excluding candidate alloy compositions in this manner it is possible to reduce the number of candidate alloy compositions for subsequent more computationally expensive calculations, thus, minimising the computational intensity of the method.

The next step involves modelling the phase equilibrium for candidate alloys within the multi-dimensional space as a function of elemental composition (I8). This determines the proportion of phases present in the alloy to predict a predicted phase equilibrium for each remaining candidate alloy composition. Predicting the proportion of phases present for one or more different combinations of state variables (examples include: temperature, pressure) and/or for a number of different phase equilibrium conditions (examples include: stable equilibrium, meta-stable equilibrium) can be used to predict the microstructure of the candidate alloys at the given condition. The state variables and/or equilibrium conditions are selected to be representative of a specific conditions of interest for the plurality of elements considered and are received by the computer as an input from a user.

For example, it may be important to know the phase equilibrium of an alloy when the state variables describe the normal service conditions for the candidate alloy. Thus, information about the candidate alloys microstructure during service is known.

The next step involves testing each candidate alloy compositions predicted phase equilibrium for one or more different combinations of state variables and/or for one or a number of different phase equilibrium conditions against the desired phase equilibrium for one or more different combinations of state variables and/or for one or a number of different phase equilibrium conditions (I9). In some instances a maximal or minimal limits to the proportion of one or more phases may be desired in order to control alloy behaviour. Alloys which do not fall within the maximal and/or minimal limits of the proportion of phases desired will be failed and excluded from the multi-dimensional alloy space (I10).

In a variation of the method it may be such that information ascertained from phase equilibrium calculations using one or more different combinations of state variables and/or for a number of different phase equilibrium conditions may be used as input to one or more subsequent merit index tests. Thus, the one or more subsequent merit index tests are performed after the phase equilibrium tests and the merit index test is a function of an aspect of the predicted phase equilibrium for the respective individual one of the plurality of candidate alloy compositions.

In an embodiment of the method, a subset (i.e. a new multi-dimensional alloy space) of the initial multi-dimensional alloy space searched may be generated (I14-I17). This subset would have newly defined upper and lower limits for each of the plurality of elements—which sit within the initial upper and lower limits—for one or more of the plurality of elements of concern. The new upper and lower bounds for the plurality of elements may be determined from the maximum and/or minimum concentrations of the plurality of elements for the remaining plurality of candidate alloy compositions after one or more merit indices have been tested and/or the phase equilibrium has been tested (I14). The subset is populated with a new plurality of candidate alloy compositions optionally with one or more of the plurality of elements being varied by a smaller increment than used in the initial multi-dimensional space searched (I16). Thus, allowing for searching for optimal solutions at a higher resolution within a more constrained multi-dimensional alloy space.

In a variation of this invention a subset of the multi-dimensional alloy space may constructed numerous times with each subsequent new multi-dimensional alloy space based upon the having upper and lower limits which fall within the previous multi-dimensional alloy spaces searched. The new multi-dimensional alloy space may be populated with candidate alloy compositions where a lower magnitude increment size for one or more of the plurality of elements is used. This iterative approach containing a feedback loop may be used to reduce the overall computational intensity of the method.

In a variation of this method the property requirements for one or a number of merit indices may be modified when a subset of the initial multi-dimensional alloy space is considered. The merit index or combination of merit indices may be modified so as to reduce and or increase the property requirements.

The next step includes reaching a point where the increments by which the compositions of the plurality of elements change between adjacent candidate alloy compositions has reached the manufacturing tolerance for the process for each individual element. This represents the final stage of the test process. As with previous iterations each candidate alloy composition within the multi-dimensional alloy space will have merit indices calculated and tested against design constraints, and optionally phase equilibrium calculations will be conducted and tested against desired phase equilibrium criteria. After all tests in this final test loop are completed all the remaining candidate alloy compositions satisfy the minimum design requirements for the new designed alloy composition.

At this point a selection algorithm can be applied to isolate the alloy composition which has the optimal balance of properties for the intended application (I12). For example, a sorting algorithm may be used to select a composition from the remaining candidate alloys which has the most desirable merit index for a given property. This may be output as the designed alloy composition.

In an embodiment, the designed alloy composition which is output is simply a list of the remaining candidate alloy compositions which have passed all tests, and/or a range of alloy compositions encompassing the remaining candidate alloy compositions.

A final step may include manufacture of an alloy with a composition within the designed alloy composition for validation and deployment (I13).

In a preferred embodiment all merit index tests which do not require as an input an output from the phase equilibrium test are performed one after another in the performing step. After those merit index tests have been performed, the method returns to the populating step where a new multi-dimensional alloy space is defined which is a subset of the (original) multi-dimensional alloy space and is based on the designed alloy composition. The new multi-dimensional alloy space is populated in the same way as described above, preferably with a modified magnitude of a difference in content of each element between adjacent candidate alloy compositions. Optionally the above mentioned at least one merit index tests which do not require an output of the phase equilibrium test are performed again. Otherwise the phase equilibrium test is performed, followed by the merit index tests which are a function of an aspect of the predicted phase equilibrium (for example lattice misfit, heat-treatment window and anti-phase boundary energy merit index tests).

Optionally the new multi-dimensional alloy space is then re-defined as many times as necessary until the output designed alloy composition is satisfactory in terms of predicted properties. At any time during this procedure the desired predicted properties may be updated. Preferably the desired predicted properties, if they are updated, are updated before or after a new multi-dimensional alloy space is defined.

The above mentioned preferred embodiment is desirable because it is computationally efficient to reduce the size of the multi-dimensional alloy space based on the low computationally intense merit index tests (which are those that do not require the results of the phase equilibrium test) and then a reduced multi-dimensional alloy space can be populated with candidate alloy compositions separated by smaller intervals in terms of composition thereby to achieve good resolution at lower computational expense than would otherwise be the case. Maintaining the same candidate alloy compositions for the merit index tests which require output from the phase equilibrium test as used for the phase equilibrium test also reduces the number of computationally intensive phase equilibrium tests which need to be performed.

Where reference is made to the method receiving an input, this may be in the form of a user input during carrying out of the method or in the form of a pre-defined parameter included in the computer coding for running the method.

Example: Designing a $2^{nd}$ Generation Single Crystal Nickel-Based Superalloy

In order to demonstrate the effectiveness of the computer assisted method for designing new alloy compositions, the method was used to isolate compositions for a new nickel-based superalloy. The design intent was to optimise the alloy composition such that it had properties equivalent to second generation nickel-based single crystal superalloys used for jet propulsion and power generation applications.

In this example merit index tests for cost, density, creep resistance, lattice misfit, heat-treatment window and anti-phase boundary energy are described. However, the present invention is not limited only to one or more of those merit index tests. The example also includes a phase equilibrium test (phase fractions). This test is optional. However, some of the merit index tests may require the results of the phase equilibrium test, even if the phase equilibrium test itself does not result in candidate alloy compositions failing or passing the phase equilibrium test.

Other merit indices are possible, one example which could be used is oxidation resistance. Oxidation resistance might be estimated simply on the amount of chromium present, for example.

The key design requirements for the new material included: a low cost relative to currently deployed second generation single crystal superalloys, improved creep strength, reduced/equivalent density, equivalent microstructural stability (i.e. substantially free from topologically closed packed (TCP) phases) and improved corrosion resistance.

In nickel-based superalloys, generally additions of chromium (Cr) and aluminium (Al) are added to impart resistance to oxidation, cobalt (Co) is added to improve resistance to sulphidisation. For creep resistance, molybdenum (Mo), tungsten (W), Co, rhenium (Re) and sometimes ruthenium (Ru) are introduced, because these retard the thermally-activated processes—such as, dislocation climb—which determine the rate of creep deformation. To promote static and cyclic strength, aluminium (Al), tantalum (Ta) and titanium (Ti) are introduced as these promote the formation of the precipitate hardening phase gamma-prime ($\gamma'$). This precipitate phase is coherent with the face-centred cubic (FCC) matrix phase which is referred to as gamma ($\gamma$).

The compositions for a number of currently deployed second generation nickel-based single crystal superalloys are listed in Table 1. These alloys are predominantly used for the manufacture of rotating/stationary turbine blades used for aircraft and gas turbine engines.

TABLE 1

Composition in atomic percent of second generation single crystal nickel-based superalloys used for turbine blade applications.

| Alloy (at. %) | Al | Cr | Co | Re | W | Ta | Mo | Ti |
|---|---|---|---|---|---|---|---|---|
| CMSX-4 | 12.6 | 7.6 | 9.3 | 1.0 | 2.0 | 2.2 | 0.4 | 1.3 |
| PWA1484 | 12.9 | 6.0 | 10.5 | 1.0 | 2.0 | 3.0 | 1.3 | 0.0 |
| ReneN5 | 13.9 | 8.1 | 8.2 | 1.0 | 1.6 | 2.3 | 1.3 | 0.0 |
| TMS-82+ | 12.2 | 5.9 | 8.2 | 0.8 | 2.9 | 2.1 | 1.2 | 0.6 |

In order to isolate an alloy composition with the desired combination of properties the computational design approach required a number of merit indices to estimate design relevant material properties. The different merit indices used to design the alloy for this specific application are listed in Table 2. The relative computational intensity of each merit index is also listed. A more detailed description of each model is now described.

TABLE 2

Overview of the relative computational intensity of each merit index used for the design of the second generation single crystal nickel-base superalloy described.

| Merit Index | Method | Computational Intensity |
|---|---|---|
| Cost | Rule of mixture | Low |
| Density | Rule of mixture | Low |

TABLE 2-continued

Overview of the relative computational intensity of each merit index used for the design of the second generation single crystal nickel-base superalloy described.

| Merit Index | Method | Computational Intensity |
|---|---|---|
| Creep resistance | Physics based modelling calculation | Low |
| Phase fractions | Phase equilibrium calculations (single temperature) | Medium |
| Lattice Misfit ($\gamma/\gamma'$) | Phase equilibrium calculations (single temperature) combined with physics based modelling calculation | Medium |
| Heat-treatment window | Phase equilibrium calculations (temperature range) | Medium |
| Anti-phase boundary energy | Phase equilibrium calculations combined with density functional theory/abinitio calculations | High |

A merit index for the cost was calculated as a function of elemental composition for an individual alloy based upon a simple rule of mixtures, where the weight fraction of the alloy element, $x_i$, is multiplied by the current raw material cost for the alloying element, $c_i$.

$$\text{Cost} = \Sigma_i x_i c_i \tag{1}$$

The estimate assumes that processing costs are identical for all alloys, i.e. that the product yield is not affected by composition.

A merit index for the density, $\rho$, was calculated as a function of elemental composition for an individual alloy using a simple rule of mixtures and a correctional factor (determined to be 1.05 for the case of nickel-based superalloys), where, $\rho_i$ is the density for a given element and $x_i$ is the atomic fraction of the alloy element.

$$\rho = 1.05[\Sigma_i x_i \rho_i] \tag{2}$$

A merit index for the creep resistance, was calculated as a function of elemental composition for an individual alloy based upon physics based calculations. A physically-based microstructure model can be invoked for the rate of accumulation of creep strain e when loading is uniaxial and along the $\langle 001 \rangle$ crystallographic direction. The equation set is $$\dot{\varepsilon}_{\langle 001 \rangle} = \frac{16}{\sqrt{6}} \rho_m \phi_p D_{\text{eff}} (1 - \phi_p)(1/\phi_p^{1/3} - 1)\sinh\left\{\frac{\sigma b^2 \omega}{\sqrt{6}\, K_{CF} kT}\right\} \tag{3}$$

$$\dot{\rho}_m = C \dot{\varepsilon}_{\langle 001 \rangle} \tag{4}$$

where $\rho_m$ is the mobile dislocation density, $\phi_p$ is the volume fraction of the $\gamma'$ phase, and $\omega$ is width of the matrix channels. The terms $\sigma$ and $T$ are the applied stress and temperature, respectively. The terms b and k are the Burgers vector and Boltzmann constant, respectively. The term $K_{CF} = 1 + 2\phi_p^{1/3}/3\sqrt{3\pi}(1-\phi_p^{1/3})$ is a constraint factor, which accounts for the close proximity of the cuboidal particles in these alloys. Equation 4 describes the dislocation multiplication process which needs an estimate of the multiplication parameter C and the initial dislocation density. The term $D_{\text{eff}}$ is the effective diffusivity controlling the climb processes at the particle/matrix interfaces.

Note that in the above, the composition dependence arises from the two terms $\phi_p$ and $D_{\text{eff}}$. Thus, provided that the microstructural architecture is assumed constant so that $\phi_p$ is fixed, any dependence upon chemical composition arises through $D_{eff}$. For the purposes of the alloy design modelling described here, it turns out to be unnecessary to implement a full integration of Equations 3 and 4 for each prototype alloy composition. Instead, a first order merit index $M_{creep}$ is employed which needs to be maximised, which is given by $$M_{creep} = \sum_i x_i / \tilde{D}_i \qquad (5)$$

where $x_i$ is the atomic fraction of solute i in the alloy and $\tilde{D}_i$ is the appropriate interdiffusion coefficient.

An estimate for phase fractions (e.g. the phase equilibrium test), lattice misfit, heat-treatment window and anti-phase boundary energy were calculated as a function of elemental composition for an individual alloy using thermodynamic modelling. In some instances, for example, lattice misfit or anti-phase boundary energy, the outputs from thermodynamic modelling calculations (e.g. the phase equilibrium test) are necessary inputs to the final merit index calculation.

For the case of designing an alloy composition for a turbine blade application thermodynamic modelling calculations are conducted at the service temperature for the new alloy (900° C.). The calculation requires that stable equilibrium is considered. From these calculations the phase equilibrium can be determined. For this particular design problem, information about the proportions of different phases (microstructure) and phase chemistry at this temperature were important.

Thermodynamic modelling can be used to determine the phase equilibrium in a multi-component, multi-phase systems by minimising the Gibbs free energy of the entire system. The modelling technique uses thermodynamic descriptions of lower order systems (e.g. unary, binary or ternary systems) to extrapolate to multi-component systems. To find the phase equilibrium state variables including alloy composition, temperature and pressure are required. Thermodynamic descriptions for the Gibbs energy of each phase in the system can be described as a function of elemental chemistry, these functions are derived from the thermodynamic descriptions of lower order systems. The thermodynamic properties of a system are modelled by relating the Gibbs energy for the entire system to the molar Gibbs energy of the different phases. Through numerical optimisation the lowest energy state can be determined. Once the appropriate solution has been determined information regarding the phase fractions, phase compositions and other thermodynamic properties can be determined.

In an alternative embodiment, the phase equilibrium test may look up the predicted phase equilibrium from a database, interpolating as necessary, or determine the predicted phase equilibrium in any other way.

In an embodiment the phase equilibrium test could alternatively or additionally use ab-initio techniques such as cluster expansion techniques to improve thermodynamic descriptions (as described by Reith, Stohr and Podloucky, for example).

In the case of single crystal superalloys which require superior resistance to creep deformation, the creep rupture life is maximised when the proportion of the precipitate hardening phase γ' lies between 60%-70%. Thus, this can be deduced from the calculated phase equilibrium. It is also necessary that the γ/γ' lattice misfit should conform to a small value, either positive or negative, since coherency is otherwise lost; thus limits are placed on its magnitude, typically ranging between +/−0.2%. The lattice misfit δ is defined as the mismatch between γ and γ' phases, and is determined according to $$\delta = \frac{2(a_{\gamma'} - a_\gamma)}{a_{\gamma'} + a_\gamma} \qquad (6)$$

where $\alpha_\gamma$ and $\alpha_{\gamma'}$ are the lattice parameters of the γ and γ' phases. In order to determine this lattice misfit the chemistry of both the γ and γ' phases must be known, in this case the phase compositions are determined using thermodynamic modelling calculations to predict the phase equilibrium.

In the case of single crystal nickel-based superalloys, it is important that they are almost completely comprised from the γ and γ' phases. Rejection of alloy on the basis of undesirable proportions of specific phases (not meeting the desired phase equilibrium) is also made from estimates of susceptibility to formation of deleterious phases, in this case the topologically close-packed (TCP) phases. The thermodynamic modelling of the phase equilibrium can predict the formation of such TCP phases, in this case the phase fraction of sigma (σ) and mu (μ)—the most common TCP phases to occur in single crystal superalloys—were calculated.

Therefore, thermodynamic modelling at a single temperature can be used to isolate all compositions in the design space which are calculated to result in a proportion of the γ' phase between 60 and 70%, which have a lattice misfit γ' of less than a predetermined magnitude and have a total proportion of undesirable TCP phases below a predetermined magnitude.

By conducting thermodynamic modelling across a range of temperatures the heat-treatment window for each alloy can be calculated. This value—measured in degrees Celsius—can be used to determine if a given alloy is amenable to conventional manufacturing processes used for the production of single crystal turbine blades. Typically the heat-treatment window must be greater than 50 degrees Celsius to allow for a solution heat treatment. The solution heat treatment is conducted in the single phase region, at this point the alloy will reside solely within the γ phase field. This solution heat treatment is necessary to homogenise the composition of the as cast alloy which may be highly segregated. In order determine the solution heat treatment window the phase equilibrium—or more specifically phase transformations—must be determined over a temperature range. The temperature at which completed dissolution of the γ' phase (known as the γ' solvus temperature) occurs must be known, as must the solidus temperature. The difference between the solidus temperature and the γ' solvus temperature will give the heat treatment window. So the heat-treatment test calculates as a function of the elemental composition of the individual one of the plurality of candidate alloy compositions the difference between the solidus temperature and the γ' solvus temperature and fails the individual one of the plurality of candidate alloy compositions if the difference between the solidus temperature and the gamma prime solvus temperature is less than 50° C. (50° C. being the desired predicted property for the heat treatment window test).

An merit index for the anti-phase boundary (APB) energy, was calculated as a function of elemental composition for an individual alloy composition by deriving a model from density functional theory. The model for APB energy relies upon input from phase equilibrium calculations made using thermodynamic modelling. This results in a model which is computationally intensive. Fault energies in the γ' phase—for example, the APB energy—have a significant influence on the deformation behaviour of nickel-based superalloys. Increasing the APB energy has been found to improve mechanical properties including, tensile strength and resistance to creep deformation. The APB energy was studied for a number of Ni—Al—X systems using density functional theory, where X represents the elements of interest for the plurality of elements considered. From this work the effect of ternary elements on the APB energy of the γ' phase was calculated. An equation can be constructed from the density functional theory calculations by using linear superposition for the effect for each ternary addition. This results in the generation of the following equation, $$\gamma_{APB} = 195 - 1.7x_{Cr} - 1.7x_{Mo} + 4.6x_W + 270.1x_{Ta} + 21.4x_{Nb} + 15x_{Ti} \quad (7)$$

where, $x_{Cr}$, $x_{Mo}$, $x_W$, $x_{Ta}$, $x_{Nb}$ and $x_{Ti}$ represent the concentrations, in atomic percent, of Cr, Mo, W, Ta, Nb and Ti in the γ' phase, respectively.

The merit indices and proportions of phases for the currently employed second generation single crystal turbine blade alloys were calculated using the range of models previously described. Estimates of the properties are listed in Table 3.

changed by increments of 5 at. %, all possible permutations for alloy composition in the Ni—Al—Cr—Co—Re—W—Ta were considered using 5 at. % increments, from this a multi-dimensional design space was populated with candidate alloy compositions. Thus, the plurality of candidate alloy compositions included for each of the plurality of elements at least 20 candidate alloy compositions with different amounts of respective element to each other. The multi-dimensional space searched is summarised in Table 4.

For each candidate alloy composition within the multi-dimensional space at least one design relevant merit index was calculated, beginning with the least computational expensive calculation. After each merit index was calculated the results were filtered based upon the desired predicted properties and/or desired predicted phase equilibrium requirements listed in the previous section. Only candidate alloy compositions which met the desired predicted properties and/or desired predicted phase equilibrium requirement remained within the multi-dimensional alloy space and were subject to subsequent, more computationally intense, merit index calculations. Overall this allowed for a rapid method for searching for optimal upper and lower compositional limits. A more detailed description of this process is now described.

TABLE 3

Calculated phase proportions and merit indices design method for 2nd generation single crystal turbine blades listed in Table 1.

| Alloy | Phase Proportions | | | | Creep Resistance | Density | Cost | $\gamma_{APB(111)}$ | γ/γ' Misfit |
| --- | --- | --- | --- | --- | --- | --- | --- | --- | --- |
| | γ' | σ | μ | σ + μ | ($m^{-2}s \times 10^{-15}$) | ($g/cm^3$) | ($/lb) | ($mJ/m^2$) | (%) |
| CMSX-4 | 0.65 | 0.004 | 0.024 | 0.028 | 7.2 | 8.7 | 59 | 311 | 0.17 |
| PWA 1484 | 0.63 | 0.000 | 0.040 | 0.040 | 7.5 | 8.9 | 62 | 318 | 0.17 |
| Rene N5 | 0.67 | 0.003 | 0.035 | 0.038 | 6.8 | 8.7 | 60 | 286 | 0.02 |
| TMS-82+ | 0.60 | 0.000 | 0.036 | 0.036 | 7.0 | 8.9 | 51 | 299 | 0.04 |

From the values listed in Table 3 it is possible to determine the minimum design requirements for the new alloy based upon the currently employed alloys. The minimum requirements or design constraints (i.e. the desired predicted properties and desired predicted phase equilibrium), listed in no particular order, include, but are not limited to;

A fraction of γ' phase between 0.6 and 0.7.
Total fraction of TCP phases less than 0.04.
A heat treatment window greater than 50 degrees Celsius.
A creep merit index of $7.5 \times 10^{-15}$ $m^{-2}s$
A density merit index of 8.8 $g/cm^3$ or less
A cost merit index of 45 $/lb or less.
An APB energy merit index of 280 $mJ/m^2$.
A lattice misfit merit index of less than +/−0.2%.

Optimisation of the New Alloy Composition

The initial step in the design process for the new second generation nickel-based single crystal superalloy involved selection of a plurality of elements. Concentrations of each element were considered between 0 and 100 atomic percent (at. %). The concentration of each alloying element was

TABLE 4

Compositional limits of the multi-dimensional space in the Ni—Al—Cr—Co—Re—W—Ta alloy systems. The multi-dimensional alloy space was populated with alloys where elements had been varied in 5 at. % increments.

| Composition (at. %) | Al | Cr | Co | Re | W | Ta |
| --- | --- | --- | --- | --- | --- | --- |
| Min | 0 | 0 | 0 | 0 | 0 | 0 |
| Max | 100 | 100 | 100 | 100 | 100 | 100 |
| Increment | 5 | 5 | 5 | 5 | 5 | 5 |

In FIG. 3 graphs are plotted to show the change in upper and lower limits for each alloying element as each individual merit index is sequentially tested with candidate alloy compositions which do not meet the design criteria becoming excluded from the multi-dimensional alloy space.

The calculation of merit indices was conducted in the order of computational intensity, beginning with the least computationally intense calculation. The order in which calculations were conducted was as follows: cost→density→creep-resistance→phase equilibrium.

For the initial multi-dimensional alloy space the plurality of alloying elements were considered with concentrations ranging between 0-100 at. %, all permutations of alloy composition within the multi-dimensional composition space were considered where the total sum of the individual elements Al, Cr, Co, Re W, Ta was less than or equal to 100%, with nickel being the balance for cases where Al, Cr, Co, Re W, Ta did not sum to 100%. After the material property requirement for the first merit index was tested (cost≤45$/lb) the maximum levels of expensive elements (Re, Ta) were significantly reduced (FIG. 3b) as these alloys did not pass the test, with the levels of Re reaching zero. A level of zero at this stage suggests that the optimal level of Re resides between 0-5 at. % (i.e. between zero and the increment magnitude).

The second merit index, density, was calculated for all candidate alloys which satisfied the cost requirement for the new alloy. Alloys which passed the test for density (density≤8.8 g/cm$^3$) remained within the multi-dimensional alloy space whilst alloys of density greater than the requirement failed the test and were removed. It was seen that the maximal limit of elements of with high density (Ta,W) was reduced (FIG. 3c), to lesser extent the level of Co was also reduced.

Application of the third merit index, creep resistance, further reduced the maximal limits of many of the alloying elements (FIG. 3d). The application of the test for the first three merit indices failed a large proportion of candidate alloy compositions for little computational expense.

The remaining candidate alloy compositions could now be evaluated using the more computationally expensive thermodynamic modelling calculations. These calculations, which predict the phase equilibrium at the service temperature, were used to test if candidate alloy compositions have the desired predicted phase equilibrium microstructure. Selection of the alloys based upon their phase equilibrium dramatically reduced the upper and lower limits for each of the alloying elements (FIG. 3e and FIG. 3f). In particular the levels of the γ' forming elements (Al,Ta) were reduced. The final upper and lower limits for each alloying elements are listed in Table 5.

TABLE 5

Upper and lower limits of the multi-dimensional alloy space which was searched using 5 at. % increments after testing against the pre-defined design requirements.

| Composition (at. %) | Al | Cr | Co | Re | W | Ta |
|---|---|---|---|---|---|---|
| Min | 15 | 0 | 10 | 0 | 0 | 0 |
| Max | 35 | 10 | 40 | 0 | 5 | 5 |

Following the identification of the upper and lower bounds which are defined in Table 5 a new multi-dimensional alloy space was generated. This new multi-dimensional alloy space was a subset of the original multi-dimensional alloy space defined in Table 4. Using the newly defined upper and lower limits for each alloying element (Table 6) a new multi-dimensional alloy space was populated with alloys where each element was varied by an increment of 1 at. %. To avoid missing outlying candidate alloy compositions the upper and lower limits were increased and reduced by the previous increment (5 at. %), respectively. Thus, considering rhenium for example, although none of the original candidate alloy compositions containing rhenium passed the merit index test for cost, when the new multi-dimensional alloy space was defined, rhenium was included in it in an amount between zero and 5 atomic %, where 5 atomic % was the previous increment. Consideration of the multi-dimensional space at 1 at. % increments enabled evaluation of composition-property relationships at a much higher resolution, thus, improving optimisation. The compositional range studied in 1 at. % increments is defined in Table 6.

TABLE 6

Limits of the new multi-dimensional composition space to be searched using 1 at. % increments.

| Composition (at. %) | Al | Cr | Co | Re | W | Ta |
|---|---|---|---|---|---|---|
| Min | 10 | 0 | 5 | 0 | 0 | 0 |
| Max | 40 | 15 | 45 | 5 | 10 | 10 |
| Increment | 1 | 1 | 1 | 1 | 1 | 1 |

Using the same procedures as described in the previous steps, the merit indices and for each candidate alloy composition were calculated in order of computational intensity, with the order being cost→density→creep-merit-index→phase equilibrium→heat-treatment window→APB energy. Inclusion of more computationally expensive calculations at this point—heat treatment window and APB energy—allowed for more stringent testing of candidate alloy compositions. In the same manner as the previous step, alloys which failed the test for a given merit index were removed from the multi-dimensional alloy space before proceeding to more computationally expensive calculations.

Although as here described the low computationally intense merit index tests are performed again after defining the new multi-dimensional space, this is not necessarily the case. It may be that after defining a new multi-dimensional space that only previously non completed merit index tests and/or phase equilibrium tests are performed. Alternatively only some of those previously performed merit index tests and phase equilibrium tests may be repeated following definition of a new multi-dimensional alloy space. Additionally or alternatively the order in which the merit index tests and phase equilibrium test are performed may be changed following definition of a new multi-dimensional alloy space.

Those tests requiring information from the phase equilibrium test are performed on the same remaining candidate alloy compositions as the phase equilibrium test, thereby avoiding the necessity to recalculate the predicted phase equilibrium.

FIG. 4 shows the evolution of the upper and lower limits of the multi-dimensional alloy space as each candidate alloy composition was tested against the set of property requirements. Comparison of the upper and lower limits defined in Table 6 (initial dataset for this step) and Table 7 (fully tested dataset for this step) illustrates the effectiveness of the optimisation method. The upper and lower limits was reduced to a very narrow range for the plurality of elements considered.

TABLE 7

Upper and lower limits of the multi-dimensional space which was searched using 5 at. % increments after application of the pre-defined property requirements.

| Composition (at. %) | Al | Cr | Co | Re | W | Ta |
|---|---|---|---|---|---|---|
| Min | 13 | 8 | 11 | 0 | 4 | 2 |
| Max | 14 | 10 | 19 | 0 | 4 | 2 |

Once narrow upper and lower limits had been identified for each of the plurality of alloying elements thereby to define a (second) new multi-dimensional alloy space it was possible to change each alloying element by an increment representative of the manufacturing tolerance achieved during the melt process used for the production of such alloys. For the plurality of elements of interest this was 0.2 at. %. The new multi-dimensional alloy space searched for the optimal composition is defined in Table 8. As with previous steps the upper and lower limits for each alloying element were broadened by the previous increment (1 at. % in this case) to account for any outlying compositions.

TABLE 8

Limits of the new multi-dimensional composition space to be searched using 0.2 at. % increments.

| Composition (at. %) | Al | Cr | Co | Re | W | Ta |
|---|---|---|---|---|---|---|
| Min | 12 | 8 | 10 | 0 | 3 | 1 |
| Max | 15 | 11 | 20 | 1 | 5 | 3 |
| Increment | 0.2 | 0.2 | 0.2 | 0.2 | 0.2 | 0.2 |

As with previous steps, calculations were conducted in order of computational intensity with alloys that did not pass each merit index test being eliminated after each merit index is calculated. Once all possible alloys which meet the initial property requirements were discovered at a resolution representative of the manufacturing tolerance it was possible to select the alloy with the optimal set of properties from the remaining dataset. That is, the desired alloy composition was output based on one or more of the individual ones of the plurality of candidate alloy compositions which passed all tests.

The designed alloy composition may be further refined for example by returning to step I1 and increasing the desired predicted properties. After performing the merit index tests and/or phase equilibrium test, the output designed alloy composition will be further narrowed.

Below a method for selecting an alloy composition is described with reference to FIG. 5. The designed alloy composition may include more than one group of candidate alloy compositions. For example, a particular set of desired predicted properties may be achieved by more than one range of compositions which are separated from each other by a gap in the range of at least one element. This would be the case, for example, if in a single dimension a predicted desired property varies as a function of elemental composition to produce two peaks (or troughs). The present method would output as the designed alloy composition a range of compositions associated with the first peak and a range of compositions associated with the second peak.

The below described method results in a single alloy composition being output by the computer assisted method. However, it is not necessary to use this method of outputting a single alloy composition as it may be equally or more desirable that the designed alloy composition represents a range of compositions which meet the desired properties.

To select an alloy composition with the best properties from the remaining alloys (i.e. those falling within the designed alloy composition) which met the initial design requirements were tested using increased property requirements until one solution remained. A flowchart outlining this selection method is given in FIG. 5.

The selection process begins by considering all the candidate alloys within the final subset of the multi-dimensional alloy space (Table 8 in this instance) which met the minimum property requirements. If there were only one alloy remaining in this dataset then it would be the optimal solution for the application.

As more than one candidate alloy composition remained a search algorithm which tested the material for increased property requirements was applied. This began by applying an individual weighting factor to each of the different merit indices (property requirements). It is also possible to have equal weighting factors for all merit indices. The sum of the weighting factors must be equal to unity. Examples of the different weighting factors used for the selection of an alloy composition for the new second generation single crystal nickel-based superalloy are listed in Table 9. For some of the material properties for example volume fraction of $\gamma'$ no weighting factor is required as it is only necessary that the volume fraction lies between the pre-determined upper and lower limits (0.6 to 0.7 in this instance).

TABLE 9

Weighting factors for different alloys selected. Alloys listed in Table 10.

| Alloy | $\gamma'$ | $\sigma$ | $\mu$ | $\sigma + \mu$ | Creep Merit Index | Density | Cost | $\gamma_{APB(111)}$ | $\gamma/\gamma'$ Misfit |
|---|---|---|---|---|---|---|---|---|---|
| Max. Balance | — | — | — | 0.2 | 0.2 | 0.2 | 0.2 | 0.2 | — |
| Min. TCP | — | — | — | 1.0 | — | — | — | — | — |
| Max. Creep | — | — | — | — | 1.0 | — | — | — | — |
| Min. Density | — | — | — | — | — | 1.0 | — | — | — |
| Min. Cost | — | — | — | — | — | — | 1.0 | — | — |
| Max. APB | — | — | — | — | — | — | — | 1.0 | — |

Following selection of the weighting factors an increment for percentage improvement was selected, the selection of this number, which must be positive, can be random. By taking the product of the percentage improvement and weighting factor a percentage improvement for each individual material property can be calculated. Thus, new more stringent property requirements can be defined.

Candidate alloys can then be tested against these new property requirements, candidate alloys which pass this new test will exceed the initial minimum design requirements. If the number of alloys remaining after the alloys have been tested against the improved property requirements is greater than one then the optimum alloy has not been found. Thus, the percentage improvement can be further increased. This process can be iterated until only one solution remains, the remaining solution is the optimum solution, see FIG. 5. The last remaining solution is the optimum alloy chemistry.

The alloy compositions shown in Table 10 correspond to the sections made based upon the different combinations of weighting factors listed in Table 9. It is seen that a different alloy composition is isolated based upon the individual requirements specified.

TABLE 10

Alloys selected from the final dataset based upon different design criteria.

| Composition (at. %) | Al | Cr | Co | Re | W | Ta |
|---|---|---|---|---|---|---|
| Equal Weight | 14.2 | 10.4 | 12.4 | 0.6 | 3.0 | 2.2 |
| Max. Creep | 13.4 | 9.8 | 13.6 | 0.6 | 3.4 | 2.0 |
| Max. APB | 13.4 | 11.0 | 13.6 | 0.4 | 3.2 | 2.6 |
| Min. Density | 14.0 | 11.0 | 13.4 | 0.4 | 3.2 | 2.0 |
| Min. Cost | 13.8 | 9.4 | 11.8 | 0.4 | 3.8 | 2.0 |
| Min. TCP | 13.4 | 8.0 | 13.6 | 0.4 | 3.4 | 2.0 |

In Table 11 the calculated properties for each of the new alloys in Table 10 are listed. These properties have been listed alongside the calculated properties for the currently deployed second generation single crystal nickel-based superalloys. The new alloy are all estimated to perform better in creep and have a lower cost. The oxidation properties of each alloy is also estimated to be better based upon the relatively higher Cr content relative to the current second generation single crystal superalloys. The alloys are also of an equivalent density and microstructural stability. Hence they exceed the performance of what is currently available.

TABLE 11

Calculated properties for the new alloys. The properties of the alloys listed in Table 1 are also included for comparison

| | Phase Fractions | | | | Creep Merit Index | Density | Cost | $\gamma_{APB(111)}$ | $\gamma/\gamma'$ Misfit |
|---|---|---|---|---|---|---|---|---|---|
| | $\gamma'$ | $\sigma$ | $\mu$ | $\sigma + \mu$ | ($m^{-2}s \times 10^{-15}$) | (g/cm³) | ($/lb) | (mJ/m²) | (%) |
| Currently Deployed Alloys | | | | | | | | | |
| CMSX-4 | 0.65 | 0.004 | 0.024 | 0.028 | 7.2 | 8.7 | 59 | 311 | 0.17 |
| PWA 1484 | 0.63 | 0.000 | 0.040 | 0.04 | 7.5 | 8.9 | 62 | 318 | 0.17 |
| Rene N5 | 0.67 | 0.003 | 0.035 | 0.038 | 6.8 | 8.7 | 60 | 286 | 0.02 |
| TMS-82+ | 0.6 | 0.000 | 0.036 | 0.036 | 7 | 8.9 | 51 | 299 | 0.04 |
| New Alloys | | | | | | | | | |
| Equal Weight | 0.67 | 0.000 | 0.040 | 0.040 | 7.7 | 8.7 | 43 | 285 | −0.043 |
| Max. Creep | 0.61 | 0.000 | 0.039 | 0.039 | 8.2 | 8.8 | 42 | 285 | −0.012 |
| Max. APB | 0.64 | 0.000 | 0.040 | 0.040 | 7.6 | 8.8 | 35 | 306 | 0.012 |
| Min. Density | 0.64 | 0.000 | 0.036 | 0.036 | 7.5 | 8.7 | 34 | 280 | −0.096 |
| Min. Cost | 0.65 | 0.000 | 0.039 | 0.039 | 7.5 | 8.8 | 33 | 281 | −0.068 |
| Min. TCP | 0.62 | 0.000 | 0.024 | 0.024 | 7.5 | 8.8 | 33 | 286 | 0.009 |

The invention claimed is:

1. A method of manufacturing an alloy, the method comprising:
   designing a designed alloy composition comprising a plurality of elements, the designing comprising the steps of:
   populating a multi-dimensional alloy space with a plurality of candidate alloy compositions, the plurality of candidate alloy compositions including for each of the plurality of elements at least three candidate alloy compositions with different amounts of the respective element to each other;
   performing tests on each individual one of the plurality of candidate alloy compositions until each of the individual ones of the plurality of candidate alloy compositions fails a test or has passed all tests;
   outputting the designed alloy composition based on one or more of the individual ones of the plurality of candidate alloy compositions which have passed all tests,
   wherein the tests on each individual one of the plurality of candidate alloy include at least:
   a phase equilibrium test in which predicted phase equilibrium is determined as a function of elemental composition of the individual one of the plurality of candidate alloy compositions; and
   at least one merit index test in which a predicted property of the individual one of the plurality of candidate alloy compositions is predicted as a function of the elemental composition of the individual one of the plurality of candidate alloy compositions and failing the individual one of the plurality candidate alloy compositions if the predicted property does not meet a desired predicted property,
   wherein in the performing step at least one merit index test is performed after the phase equilibrium test and is a function of an aspect of the predicted phase equilibrium for the respective individual one of the plurality of candidate alloy compositions, and
   wherein the phase equilibrium test further comprises failing the individual one of the plurality of candidate alloy compositions if the predicted phase equilibrium does not meet a desired predicted phase equilibrium; and
   manufacturing the alloy with a composition within the designed alloy composition.

2. The computer assisted method of claim 1, wherein in the performing step the plurality of tests are performed one after the other in an order starting with the least computationally intensive test.

3. The method of claim 1, further comprising receiving an input indicative of the desired predicted phase equilibrium.

4. The method of claim 1, further comprising receiving an input indicative of at least one temperature and/or pressure at which the predicted phase equilibrium is determined and/or an input indicative or whether stable equilibrium of meta-stable equilibrium phase fractions are to be calculated.

5. The method of claim 1, further comprising receiving an input indicative of a desired predicted property for each of the at least one merit index tests.

6. The method of claim 1, further comprising receiving an input relating to which elements make up the plurality of elements and/or maximum and/or minimum content of at least one of the elements of the plurality of elements, thereby to define the limits of the multi-dimensional alloy space.

7. The method of claim 1, further comprising receiving, for at least one element of the plurality of elements, an input relating to a magnitude of a difference in content of that element between adjacent candidate alloy compositions.

8. The method of claim 1, further comprising the step of carrying out the populating step on a new multi-dimensional alloy space to define a new plurality of candidate alloy compositions and carrying out the performing and outputting steps on the new plurality of candidate alloy compositions.

9. The method of claim 8, wherein the new multi-dimensional alloy space is a subset of the multi-dimensional alloy space and is based on the designed alloy composition.

10. The method of claim 8, wherein the carrying out further includes receiving an input relating to maximum and/or minimum content of at least one of the elements of the plurality of elements thereby to define the limits of the new multi-dimensional alloy space as a subset of the multi-dimensional alloy.

11. The method of claim 8, further comprising:
receiving, for at least one element of the plurality of elements, an input indicative of a modified magnitude of a difference in content of that element between adjacent candidate alloy compositions of the new multi-dimensional alloy space.

12. The method of claim 8, further comprising:
receiving an input indicative of a modification to the desired predicted property of at least one of the at least one merit index tests and/or receiving an input indicative of a modification to the desired phase equilibrium.

13. The method of claim 8, further comprising repeating the populating, performing, outputting and carrying out steps.

14. The method of claim 1, wherein the at least one merit index test predicts:
a cost of candidate alloy compositions;
a density of candidate alloy compositions;
an anti-phase boundary energy of candidate alloy compositions;
a lattice misfit of candidate alloy compositions;
creep properties of candidate alloy compositions; or
a heat treatment window of candidate alloy compositions, or combinations thereof.

15. The method of claim 1, wherein the phase equilibrium test predicts a total fraction of a given phase of candidate alloy compositions.

* * * * *